US009351983B2

(12) United States Patent
Corda et al.

(10) Patent No.: US 9,351,983 B2
(45) Date of Patent: May 31, 2016

(54) USE OF GLYCEROPHOSPHOINOSITOLS FOR THE TREATMENT OF SEPTIC SHOCK

(71) Applicant: CONSIGLIO NAZIONALE DELLE RICERCHE, Rome (IT)

(72) Inventors: Daniela Corda, Rome (IT); Pasquale Zizza, Rome (IT); Alberto Luini, Rome (IT); Stefania Mariggio', Rome (IT)

(73) Assignee: CONSIGLIO NAZIONALE DELLE RICERCHE, Rome (RM) (IT)

( * ) Notice: Subject to any disclaimer, the term of this patent is extended or adjusted under 35 U.S.C. 154(b) by 0 days.

(21) Appl. No.: 14/433,406

(22) PCT Filed: Oct. 4, 2013

(86) PCT No.: PCT/EP2013/070728
§ 371 (c)(1),
(2) Date: Apr. 3, 2015

(87) PCT Pub. No.: WO2014/053642
PCT Pub. Date: Apr. 10, 2014

(65) Prior Publication Data
US 2015/0272971 A1    Oct. 1, 2015

(30) Foreign Application Priority Data

Oct. 4, 2012  (IT) .............................. RM2012A0473

(51) Int. Cl.
*A61K 31/66*  (2006.01)
*A61K 31/683*  (2006.01)

(52) U.S. Cl.
CPC .................................. *A61K 31/683* (2013.01)

(58) Field of Classification Search
USPC .......................................................... 514/148
See application file for complete search history.

(56) References Cited

U.S. PATENT DOCUMENTS

| 2010/0048492 A1 | 2/2010 | Quesniaux Ryffel et al. |
| 2011/0224162 A1 | 9/2011 | Quesniaux Fyffel et al. |

FOREIGN PATENT DOCUMENTS

| CA | 2427352 | * | 5/2002 |
| EP | 1 023 902 A1 | | 8/2000 |
| WO | 02/09678 A2 | | 2/2002 |
| WO | 02/38575 A1 | | 5/2002 |
| WO | 03/087109 A1 | | 10/2003 |

OTHER PUBLICATIONS

Doerfler et al., J. Clin. Invest. 1994;93:1583-1591.*

* cited by examiner

*Primary Examiner* — San-Ming Hui
(74) *Attorney, Agent, or Firm* — Lucas & Mercanti, LLP.

(57) ABSTRACT

The present invention refers to glycerophosphoinositols (GPIs) and derivatives thereof for use in the treatment of pathologies related to a Lipopolysaccharide (LPS)-activated tissue-factor (TF) activity, as pathologies induced by high bacteremia, i.e. septic shock.

6 Claims, 19 Drawing Sheets

USE OF GLYCEROPHOSPHOINOSITOLS FOR THE TREATMENT OF SEPTIC SHOCK

CROSS-REFERENCE TO RELATED APPLICATIONS

This application is a 371 of PCT/EP2013/070728, filed Oct. 4, 2013, which claims the benefit of Italian Patent Application No. RM2012A000473, filed Oct. 4, 2012.

FIELD OF THE INVENTION

The present invention relates to glycerophosphoinositols (GPIs) and derivatives thereof for use in the treatment of pathologies related to a Lipopolysaccharide (LPS)-activated tissue-factor (TF) activity, as pathologies induced by high bacteremia, i.e. septic shock.

BACKGROUND OF THE INVENTION

Sepsis syndrome (sepsis) is an adverse systemic response to infection that includes low blood pressure, rapid heartbeat and respiration, fever, and organ dysfunction associated with compromised blood circulation. Sepsis can occur through infection by Gram-positive bacteria and even fungi and viruses, or as a consequence of secreted toxins. However, the sepsis syndrome occurs commonly in response to lipopolysaccharides (LPS; also known as endotoxin) from Gram-negative bacteria. LPS is a major constituent of Gram-negative bacterial cell wall and is essential for membrane structure and integrity. The portion of LPS that causes shock is the innermost and most highly conserved phosphoglycolipid, lipid A, which acts by inducing robust inflammatory responses. Over the years, many LPS-binding proteins have been identified on monocytes/macrophages and other LPS-responsive cell types. The identification of CD14, a GPI-anchored protein, as a cell-associated LPS binding protein, represents the first step in the understanding of LPS signalling. However, as CD14 lacks a trans-membrane signalling domain, the involvement of accessory receptor was supposed. Quite recently, several members of the highly conserved family of Toll-like receptor (TLR) proteins were identified as the putative co-signalling molecules for CD14. TLR4 may be an LPS signaling molecule as first suggested by the finding that a constitutively active form of TLR4 resulted in activation of LPS-induced NF-κB-mediated signalling. In addition to TLR4, also TLR2 has been implicated in cellular response to LPS. However, analysis of mice with targeted disruptions in their tlr2 or tlr4 genes revealed that TLR4 knockouts, but not TLR2 ones, are LPS unresponsive, whereas TLR2 appears to be essential for the response to other non-LPS bacterial cell wall products. Following the initial host-pathogen interaction there is a widespread activation of the innate immune response, the purpose of which is to coordinate a defensive response involving both humoral and cellular components. Mononuclear cells play a key role in LPS response, releasing pro-inflammatory cytokines and a host of other small molecules. TNFα and IL-1 are the prototypic inflammatory cytokines that mediate many of the cellular events related to LPS exposure. They are rapidly released (30-90 minutes) after exposure to LPS and in turn amplify the inflammatory response. In addition, several other cytokines, including IL-1 and IL-6, are potent inducers of coagulation. Disorders of coagulation are common in sepsis, and in a certain number of cases (30-50% of patients) also evolve in a more severe clinical form, disseminated intravascular coagulation. In sepsis, LPS (or other bacterial components) initiate coagulation cascade through induction of tissue-factor (TF) expression on mononuclear and endothelial cells. TF in turn activates a proteolytic cascade (coagulation cascade), which finally leads to the conversion of pro-thrombin into thrombin, and consequent activation of fibrin. The net result of this sequence of events is the deposition of fibrin clots in small blood vessels with consequent reduction of tissue perfusion, multiple organ failure and, in several cases, death. The robust inflammatory response that occurs in sepsis is usually balanced by an array of regulatory molecules that attempt to restore immunological equilibrium. Counter-inflammatory molecules include cytokine antagonists such as the soluble TNFα receptors and IL-1 receptor, inactivators of the coagulation cascade and anti-inflammatory cytokines, of which IL-10 is the prototype. Despite this, anti-LPS and anti-TNFα antibodies, soluble TNFα receptors, IL-1Ra and corticosteroids have all failed to alter the outcome of septic shock. A slightly success has been achieved with activated protein C, an anti-thrombotic, anti-inflammatory, serine protease activated by thrombin and consumed during sepsis. Levels of activated protein C are inversely correlated with the probability of death from sepsis, and replacement of activated protein C can reduce the relative risk of death during severe sepsis by almost 20%.

However, it is not known at this time of any pharmacological treatment able to efficiently counteract the sepsis. Here, authors describe a new class of potent and selective anti-inflammatory and anti-thrombotic molecules: the glycerophosphoinositols. Glycerophosphoinositols are natural occurring phosphoinositide metabolites produced by the activity of the α isoform of group IV phospholipase $A_2$ ($PLA_2IV\alpha$) through two sequential deacylation reactions. Although elevated levels of glycerophosphoinositols have been historically associated with the expression of oncogenic Ras, these molecules are detectable in all cell types and their production is increased in response to a large variety of stimuli, both pharmacological (e.g. calcium ionophores) and receptor-mediated (e.g. EGF, ATP and norepinephrine). Glycerophosphoinositols are found both within the cell and in the extracellular space, where they are released via a transporter, Glut-2, characterized both in yeast and in mammalian cells. Glycerophosphoinositols have been found to affect a plethora of cellular functions, ranging from inhibition of adenylyl cyclase, with consequent modulation of thyroid cell growth and iodide uptake, to reorganisation of the actin cytoskeleton in fibroblasts.

Recently, authors have reported a new role of glycerophosphoinositols in modulation of immune response (Zizza et al., J Biol Chem. 2012 May 11; 287(20):16849-59; Corda et al., Biochem Soc Trans. 2012 February; 40(1):101-7; Patrussi et al., Cell Signal. 2007 November; 19(11):2351-60). In T-lymphocyte, indeed, exogenously added glycerophosphoinositols synergise with the chemotactic factor, sdf-1α, by increasing the rate of cell migration.

WO 03/087109 refers to glycerophoshoinositol for the treatment of pathologies mediated by the activation or overstimulation of enzymatic and metabolic G protein associated pathways, as e.g. septical shock.

WO 02/38575 discloses the use of derivatives and analogues of the glycero-phospho-D-myo-inositol optionally O-substituted for the treatment of pathologies mediated by the activation or over-stimulation of $PLA_2IV\alpha$.

Though both WO 03/087109 and WO 02/38575 mention and claim septic shock, no data are provided even merely suggesting the true therapeutic activity of the compounds.

Authors have now found a new mechanism of action for the onset of sepsis, severe sepsis or septic shock related to a Lipopolysaccharide (LPS)-activated tissue-factor (TF) activity. Authors have found that the stimulus by LPS of TLR receptor is not mediated by PLA$_2$IVα. It has in fact been shown that TF activity is inhibited by GPIs but not by pyrrofenone (a classic inhibitor of PLA$_2$IVα) and thus GPIs can be used to treat septic shock by inhibiting TF activity.

US2010/048492 and US2011/224162 refer to the use of glygerophopshoinositol derivatives for the treatment of pathologies related to overexpression of TNFα. The instant invention refers to the LPS activation of a different factor, TF.

Despite such detailed investigations, there is still the need of a safe and effective agent able to treat, prevent or reduce the severity of a symptom of a pathology comprised in the group of: sepsis, severe sepsis, or septic shock.

SUMMARY OF THE INVENTION

Sepsis describes a complex clinical syndrome that results from a harmful or damaging host response to infection. Inflammatory cytokines and pro-coagulants in monocytes/macrophages have a key role in physiological and pathological inflammatory responses. Both positive and negative signals regulate the expression of inflammatory genes committed to restore the normal homeostasis after acute inflammation. However, the physiological mediators involved in this process are poorly defined (Fujiwara N and Kobayashi K, Curr Drug Targets Inflamm Allergy. 2005 June; 4(3):281-6). Recent investigations have revealed the active involvement in the inflammatory response of phosphoinositide derivatives produced by phospholipase A$_2$ activity: the glycerophosphoinositols (GPIs) (Zizza et al., J Biol Chem. 2012 May 11; 287(20):16849-59; Corda et al., Biochem Soc Trans. 2012 February; 40(1):101-7; Patrussi et al., Cell Signal. 2007 November; 19(11):2351-60). Immune cells have a potent and regulated phospholipase A$_2$ that provides fine modulation of intracellular glycerophosphoinsitol (GroIns) levels consequent to cell development, differentiation and hormone stimulation [i.e. exposure to lipopolysaccharides (LPS), cytokines, and other pro-inflammatory agents] (Corda et al. Biochim Biophys Acta. 2002 May 23; 1582(1-3):52-69; Corda et al., Cell Mol Life Sci. 2009 November; 66(21):3449-67).

It is herein delineated a role of the GPIs as endogenous metabolites that are part of a negative feed-back loop that limits pro-inflammatory and pro-thrombotic responses in human monocytes stimulated with LPS. The pro-coagulant activity of LPS-stimulated monocytes is mainly ascribed to tissue-factor expression; in addition, LPS induces increases in the mRNA levels of tissue factor, cyclooxygenase-2, interleukin-1beta (IL-1β), and tumour necrosis factor-alpha (TNFα). Pre-treatment of monocytes with GroPIns or GroPIns4P before LPS addition resulted in dose-dependent inhibition of tissue-factor activity as well as of mRNA levels of all the analysed inflammatory genes. The inhibitory effects of the two compounds show different kinetics, suggesting distinct targets for these metabolites.

Authors have investigated the effect of glycerophosphoinositols in a model of sepsis: circulating monocytes purified from healthy donors were exposed to LPS from *Escherichia coli* both in presence and in absence of glycerophosphoinositols, and the markers of sepsis were analysed. Interestingly, the glycerophosphoinositols show a robust effect in counteract the immunophatological features of endotoxin by regulating in a negative manner the expression of pro-inflammatory and pro-thrombotic genes that are, all, under the control of the transcription factor NF-κB.

To define the mechanism of action of the GPIs, authors analyzed different steps of the LPS signalling pathway in monocytes. Notably, treatment with the GPIs was consistently associated with decreased LPS-induced nuclear translocation of transcription factors, such as NF-κB. The time courses of the effects of these two GPIs on NF-κB nuclear levels were consistent with the different timing for the modulation of mRNA levels of the inflammatory markers.

The present results provides new insight into the biology of the GPIs, suggesting that these compounds, that are mainly produced by inflammatory cells, have roles as endogenous anti-inflammatory mediators for inflammation resolution and their mechanisms of action appear to be related to their reduction of nuclear accumulation of NF-κB transcription factors.

Authors have now found that the stimulus by LPS of TLR receptor is not mediated by PLA$_2$IVα. It has in fact been shown that TF activity is inhibited by GPIs but not by pyrrofenone (a classic inhibitor of PLA$_2$IVα). GPIs include phosphorylated and unphosphorylated (GroPIns) forms of GPI.

It has been found that GPIs can be used to treat septic shock by inhibiting TF activity.

Object of the invention is glycerophosphoinositols (GPIs) and derivatives thereof for use in treating, preventing or reducing the severity of a symptom of sepsis, severe sepsis or septic shock related to a Lipopolysaccharide (LPS)-activated tissue-factor (TF) activity.

Another object is glycerophosphoinositols (GPIs) for use in treating, preventing or reducing the severity of a symptom of sepsis, severe sepsis or septic shock related to a Lipopolysaccharide (LPS)-activated tissue-factor (TF) activity.

In a preferred embodiment, said sepsis, severe sepsis or septic shock is not mediated by an activation or over-stimulation of cPLA$_2$, PLA$_2$IVα or any other iso form.

Preferably, said sepsis, severe sepsis or septic shock is induced by high bacteremia.

The above derivative of glycerophosphoinositols (GPIs) is preferably glycerophosphoinositol 4-phosphate (GroPIns4P) or glycerophosphoinositol 4,5-bisphosphate (GroPIns4,5P$_2$).

The above symptom of sepsis, severe sepsis or septic shock related to a Lipopolysaccharide (LPS)-activated tissue-factor (TF) activity preferably comprises a disorder of coagulation and/or a disseminated intravascular coagulation.

The glycerophosphoinositols (GPIs) and derivatives thereof for use according to the invention, are preferably to be administered to a mammal in one or more of the following periods:

(a) prior to the onset of sepsis;
(b) during initial sepsis but before the onset of severe sepsis;
(c) during severe sepsis but before the onset of septic shock;
(d) after the onset septic shock.

For glycerophosphoinositol it is intended the compound having the following formula (II):

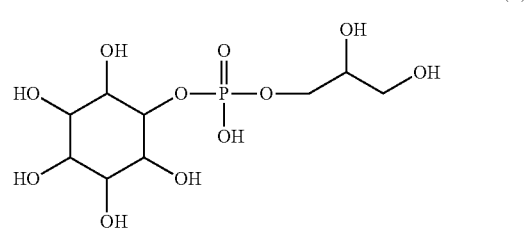

For "derivatives of glycerophosphoinositols (GPIs)" are also intended the compounds as defined in WO 0238575, as follows:

compounds of general formula (I):

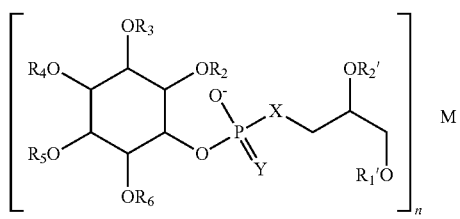

their enantiomers, diastereoisomers, racemes, their mixtures, their hydrates and solvates, wherein:

I) R', R2', R2, R3, R4, R5, R6 which can be equal or different among each other, being:

a) H or b) a group C(O)A, acylic residue of mono-carboxylic acid or emiacylic residue of di-carboxylic acid, where A can be:

a saturated or unsaturated, straight or branched aliphatic radical having from 1 to 4 double bonds, or a mono or poly-cyclic alkyl or alkenyl group, or an aryl, arylalkyl or heterocyclic group having one or more heteroatoms; these groups are optionally substituted with one or more groups selected among keto, hydroxy, acylamido, halogen, mercapto, alkylthio or alkyldithio, —COOH and these —COOH are optionally in the salt form —COOM, wherein M has the same meaning described at point (II); or c) a group B wherein B is a saturated or unsaturated, straight or branched aliphatic group with from 1 to 6 double bonds, or a mono or poly-cyclic alkyl or alkenyl group or an aryl, alkylaryl group or a heterocycle having one or more heteroatoms; these groups are optionally substituted with one or more groups selected among keto, hydroxy, acylamido, halogen, mercapto, alkylthio or alkyldithio, —COOH and these —COOH are optionally in the salt form —COOM, wherein M has the same meaning described at point (II);

(II) M is the cation of a pharmacologically acceptable inorganic element, or a cation of a pharmacologically acceptable organic base having valence n+ wherein n has the meaning described in the following point (III);

(III) n is 1 or 2 or 3;

(IV) X e Y equal or different among each other are O or S;

and wherein, when Y is S, the compounds according to formula (I) include also the respective not-neutralized compounds.

The compounds according to the invention also include non-salified derivatives thereof.

For "glycerophosphoinositol 4-phosphate" it is intended the compound having the following formula (III):

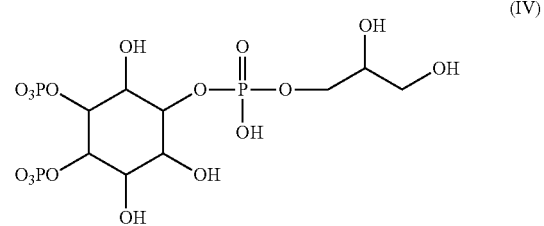

For "glycerophosphoinositol 4,5-bisphosphate" it is intended the compound having the following formula (IV):

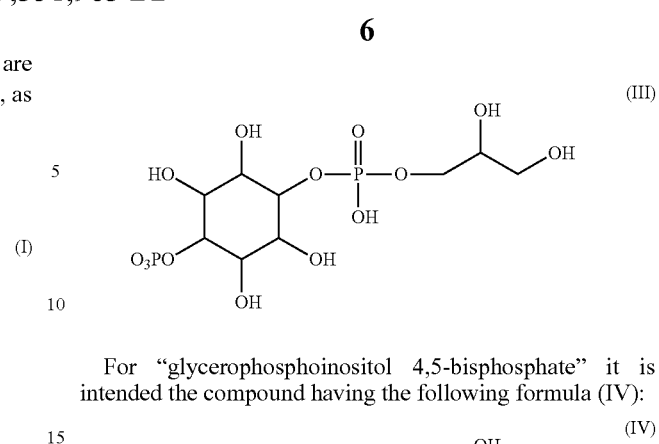

According to the present invention, preferred derivatives of glycerophosphoinositols (GPIs) are:

GPI derivatives modified at the level of the oxydryl groups, as e.g. the following compounds:

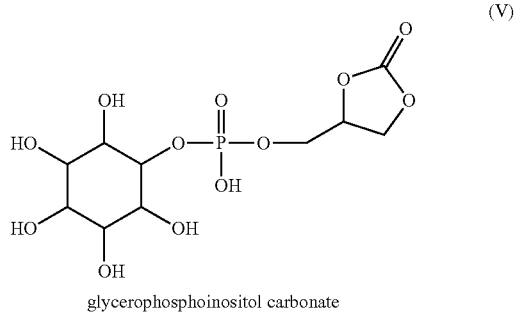

glycerophosphoinositol carbonate

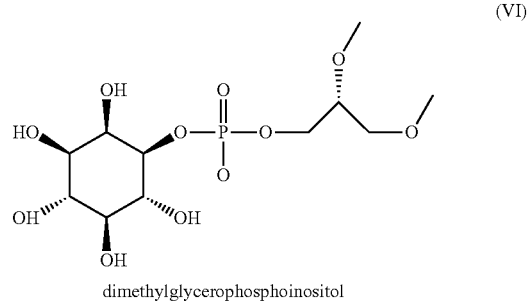

dimethylglycerophosphoinositol
DMGPIns

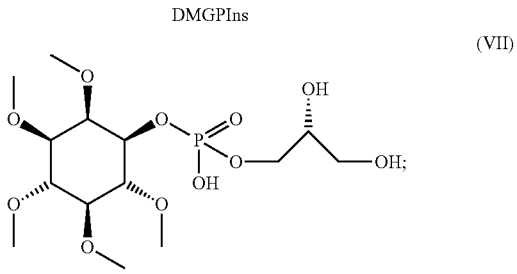

inositol-pentamethyl derivative of GroPIns
GPIns-2,3,4,5,6-OMe

GPI derivatives modified at the level of the phosphodiester bond, as e.g. the following compounds:

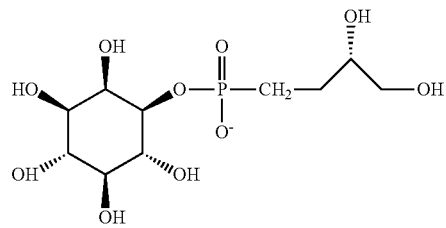

CGPIns (VIII)

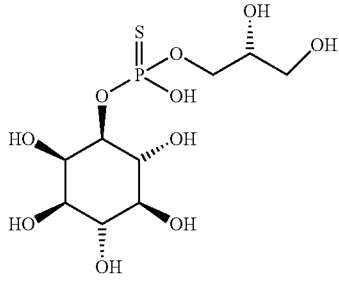

GTPIns (IX)

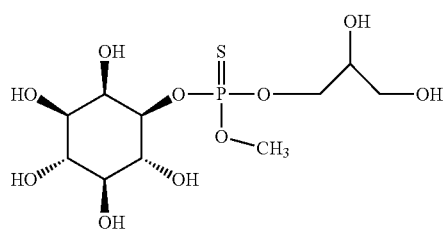

GTPIns-OMe (X)

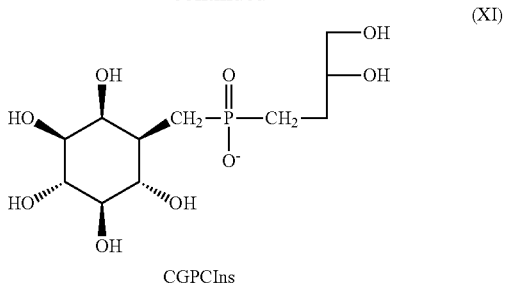

CGPCIns (XI)

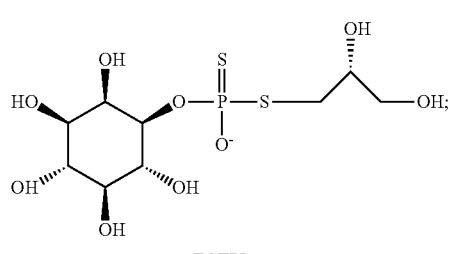

TGTPIns (XII)

analog modifications on the phosphodiester bond on the position 4 of GroPIns4P, as e.g. the following compound:

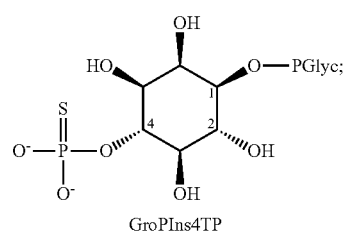

GroPIns4TP (XIII)

GPI biotinylated derivatives on different positions, as e.g. the following compounds:

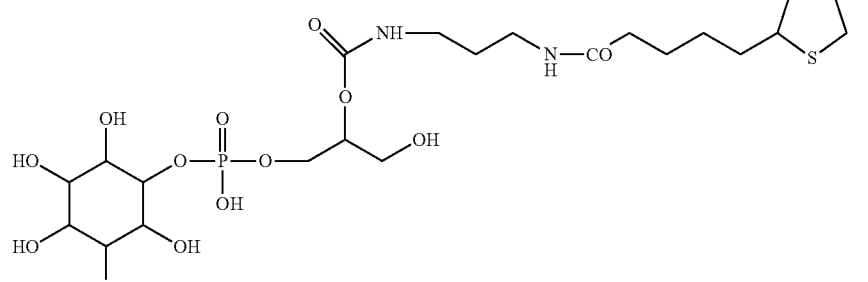

GroPIns 2-biotin (XIV)

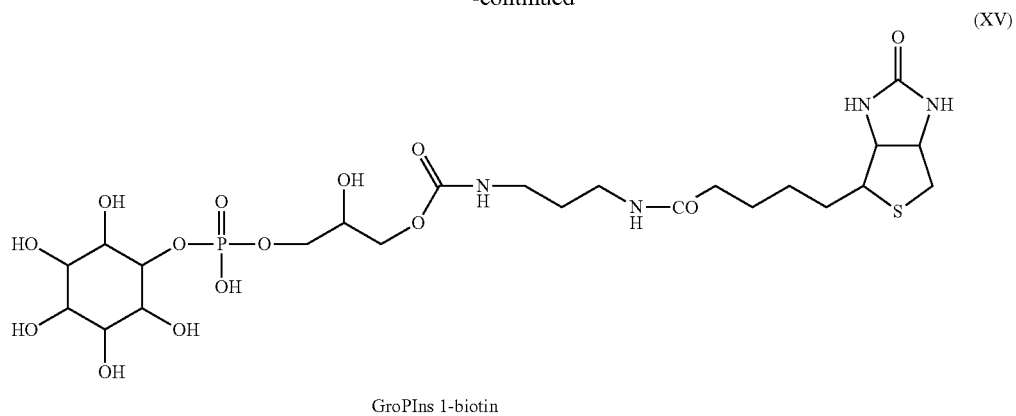

GroPIns 1-biotin

GPI modified with the insertion of fluophores, as e.g. the following compounds:

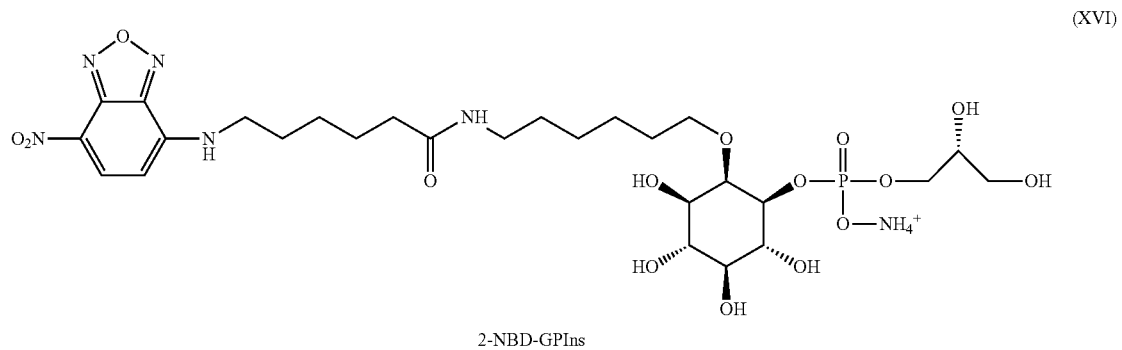 [SMILES: [NH3+]OP(=O)(OC[C@H](O)CO)O[C@H]1[C@H](O)[C@@H](O)[C@H](O)[C@@H](O)[C@H]1OCCCCCCNC(=O)CCCCCNc1ccc([N+](=O)[O-])c2nonc12]

2-NBD-GPIns ammonium salt of D-1-[(R)-sn-glycero-3-phospho]-2-O-(6-(7-nitrobenzo[1,2,5]oxadiazol-4-yl)amino)exanamido)exyl)-myo-inositol;

GPI derivatives phosphorylated on the different positions of the inositol group, as e.g. the following compounds:

and GPI diastereoisomers at the level of the different chiral centers, as e.g. the following compounds:

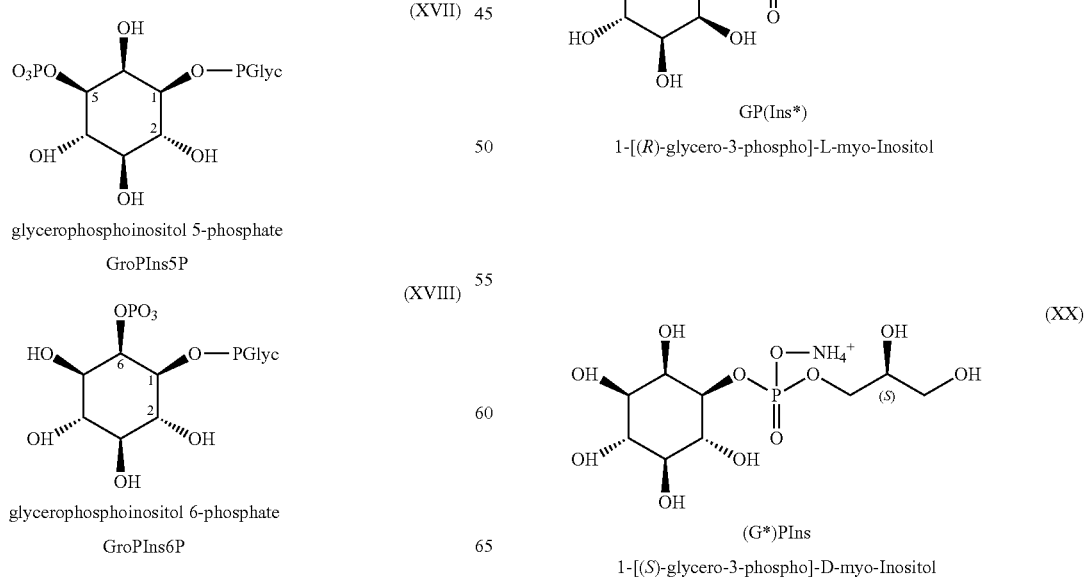

glycerophosphoinositol 5-phosphate
GroPIns5P
(XVII)

glycerophosphoinositol 6-phosphate
GroPIns6P
(XVIII)

GP(Ins*)
1-[(R)-glycero-3-phospho]-L-myo-Inositol
(XIX)

(G*)PIns
1-[(S)-glycero-3-phospho]-D-myo-Inositol
(XX)

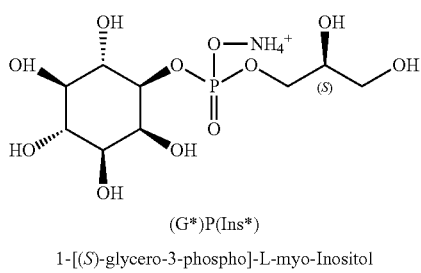

(G*)P(Ins*)

1-[(S)-glycero-3-phospho]-L-myo-Inositol

It is also an object of the invention a method of treating and/or preventing and/or reducing the severity of a symptom of sepsis, severe sepsis or septic shock related to a Lipopolysaccharide (LPS)-activated tissue-factor (TF) activity comprising administering a therapeutically effective amount of Glycerophosphoinositols (GPIs) and/or derivatives thereof as described above. The Glycerophosphoinositols (GPIs) and/or derivatives thereof composition should be formulated, dosed, and administered in a fashion consistent with good medical practice. The Glycerophosphoinositols (GPIs) and/or derivatives of the present invention can be administered by any appropriate route. This includes (but is not limited to) intraperitoneal, intramuscular, intravenous, subcutaneous, intraarticular, intratracheal, oral, enteral, parenteral, intranasal or dermal administration. The "therapeutically effective amount" of Glycerophosphoinositols (GPIs) and/or derivatives thereof to be administered is the minimum amount necessary to prevent, ameliorate, or treat a disease or disorder. The Glycerophosphoinositols (GPIs) and/or derivatives thereof need not be, but are optionally formulated with one or more agents currently used to prevent or treat the disorder in question. The effective amount of such other agents depends on the amount of Glycerophosphoinositols (GPIs) and/or derivatives thereof present in the formulation, the type of disorder or treatment, and other factors.

BRIEF DESCRIPTION OF THE DRAWINGS

The present invention will be described by means of non limiting examples referring to the following figures.

DETAILED DESCRIPTION OF THE INVENTION

Example 1

Materials and Methods

Materials

Figure 1:
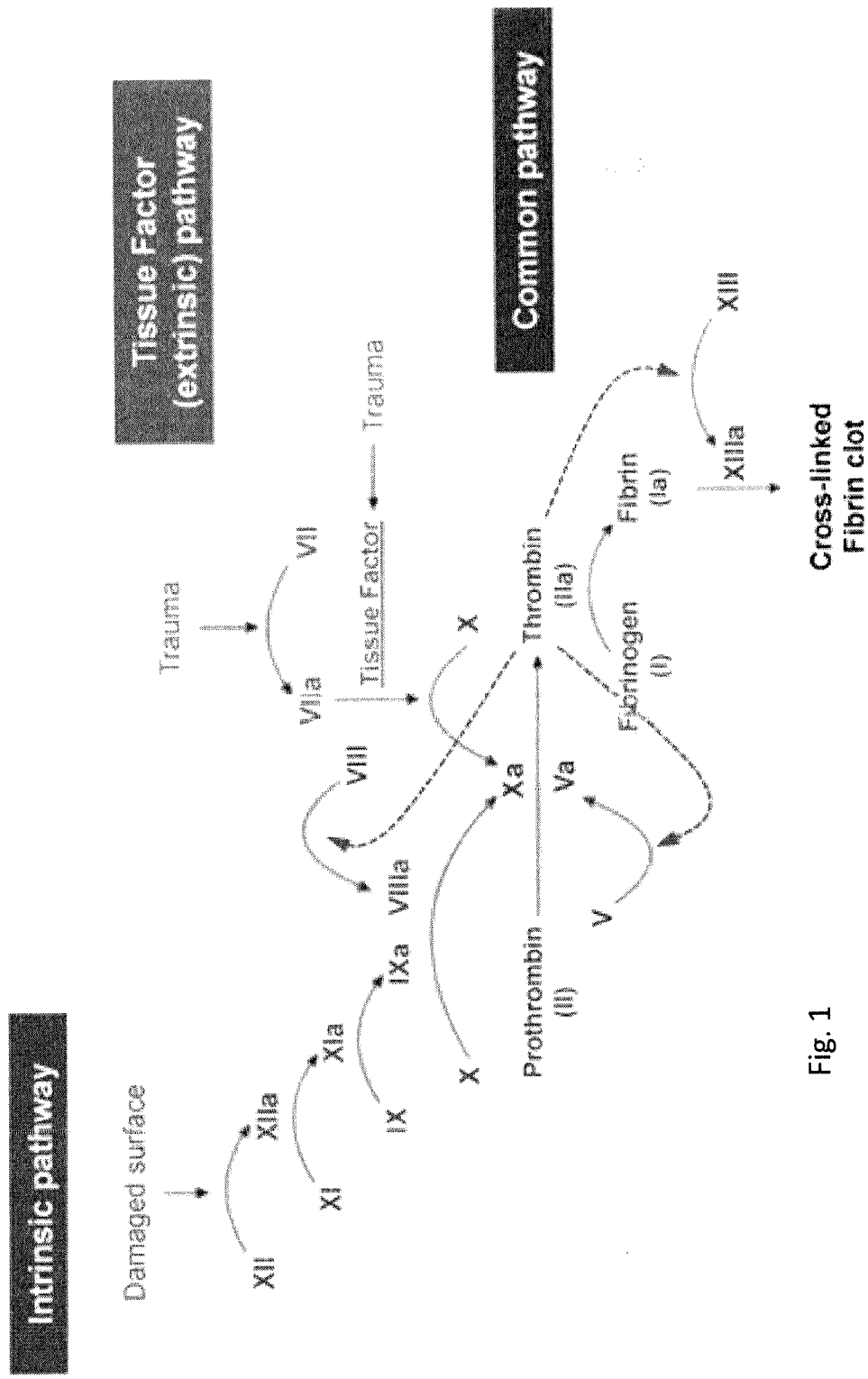
FIG. 1—The coagulation cascade. Schematic representation of the signalling pathways of the coagulation cascade. The coagulation cascade is formed by two different pathways: the intrinsic pathway (violet), which is activated by contact between blood and damaged surfaces, and the extrinsic pathway (red), which is initiated upon vascular injury (trauma). Both of the cascades are characterised by a series of reactions in which a zymogen is activated to catalyse the next reaction in the cascade. The two pathways converge in the common pathway (blue), which is initiated by the activation of factor X, to Xa. Factor Xa has a role in the further activation of pro-thrombin to thrombin. The role of thrombin is to convert fribrinogen to fibrin and to activate factor XIII. Factor XIIIa cross-links fibrin polymers, solidifying the clot. In addition, thrombin can activate factors VIII and V, furthering the signal cascade (dotted green arrow). Coagulation factors are indicated by Roman numerals, with lowercase 'a' added to indicate an active form. The coagulation factors are generally serine proteases, although with some exceptions; e.g., factor VIII and factor V are glycoproteins, and factor XIII is a transglutaminase.

Pyrrophenone was generously provided by Dr K. Seno (Shionogi Research Laboratories, Shionogi & Co. Ltd., Osaka, Japan) (Ono et al., Biochem J. 2002 May 1; 363(Pt 3):727-35). GroPIns, GroPIns4P and $GroPIns4,5P_2$ were provided by Echelon Biosciences Inc. (UT, USA).

Real-Time Reverse Transcriptase Polymerase Chain Reaction (RT-PCR)

One μg total RNA (extracted through thiocyanate/caesium chloride method) was converted to cDNA using Moloney murine leukaemia virus reverse transcriptase (Applied Biosystems, Italy). Then, 20 μl of a mix containing 10 ng cDNA, 50 nM primers (see Table 1) and SYBR Green master mix (Applied Biosystems, Italy) were used for real-time PCR. Real-time PCR measurements were performed using a PRISM 7500 Fast Real-Time PCR System (Applied Biosystems, Italy). Each sample was measured in triplicate and the data were analysed with the SDS 2.0 software (Applied Biosystems, Italy) by the delta-delta method (2-DDCT) for comparing relative expression results. Resting cells were considered the reference sample, and glyceraldehyde-3-phosphate dehydrogenase (GAPDH) served as the house-keeping gene.

TABLE 1

List of primers used in Real-Time RT-PCR

| Name | Sequence (5'-3') | Company | Concentration/ purification | SEQ ID No. |
|---|---|---|---|---|
| TF (forward) | cga tga ttc cct ccc gaa ca | Sigma-Aldrich | 200 nmol/ HPLC | SEQ ID No. 1 |
| TF (reverse) | tgc ctt tct aca act gtg tag ag | Sigma-Aldrich | 200 nmol/ HPLC | SEQ ID No. 2 |
| TNFα (forward) | gct gat ggc cct aaa cag atg a | Sigma-Aldrich | 200 nmol/ HPLC | SEQ ID No. 3 |
| TNFα (reverse) | cag agg gca gag gtc cag g | Sigma-Aldrich | 200 nmol/ HPLC | SEQ ID No. 4 |

TABLE 1-continued

List of primers used in Real-Time RT-PCR

| Name | Sequence (5'-3') | Company | Concentration/ purification | SEQ ID No. |
|---|---|---|---|---|
| IL-1β (forward) | gct gat ggc cct aaa cag atg a | Sigma-Aldrich | 200 nmol/ HPLC | SEQ ID No. 5 |
| IL-1β (reverse) | agg ctt gtc act cgg ggt t | Sigma-Aldrich | 200 nmol/ HPLC | SEQ ID No. 6 |
| COX-2 (forward) | ttc cag atc cag agc tca tta aa | Sigma-Aldrich | 200 nmol/ HPLC | SEQ ID No. 7 |
| COX-2 (reverse) | ccg gag cgg gaa gaa ct | Sigma-Aldrich | 200 nmol/ HPLC | SEQ ID No. 8 |
| GAPDH (forward) | caa ctt tgg tat cgt gaa agg ac | Sigma-Aldrich | 200 nmol/ HPLC | SEQ ID No. 9 |
| GAPDH (reverse) | aca gtc ttc tgg gtg gca gtg | Sigma-Aldrich | 200 nmol/ HPLC | SEQ ID No. 10 |

Western Blotting

Protein extracts were analysed by Western blotting by the following procedures. The nitrocellulose filters containing the proteins of interest were incubated in the blocking solution for Western blotting plus 3% bovine serum albumin (BSA) or 5% milk powder (Fluka, Switzerland) for 1 h at room temperature, and then with the primary antibody diluted to its working concentration (see Table 2) in the blocking solution for Western blotting (plus BSA or milk powder). After a 2-4 h incubation at room temperature, or an overnight (O/N) incubation at 4° C., the antibody was removed and the strips were washed twice in Tween®/Tris-buffered salt solution (TTBS), for 15 min each. The strips were next incubated for 1 h with the appropriate horse radish peroxidase (HRP)-conjugated secondary antibody (diluted 1:5,000) in the blocking solution for Western blotting (plus 5% milk powder) and washed three times in TTBS, for 10 min each, and once in TBS for 5 min. After washing the strips were incubated with the enhanced luminescence (ECL) reagents (Amersham Pharmacia Biotech, NJ, USA), according to the manufacturer instructions, and protein signals were detect by autoradiography using Kodak film.

TABLE 2

List of antibodies used in Western, blotting experiments

| Antibody | Dilution | Animal source | Company or other source |
|---|---|---|---|
| PLA₂IVα | 1:5,000 | Rabbit | homemade (Zizza et al., 2012) |
| phospho-p38 | 1:1,000 | Rabbit | Cell Signaling |
| p38 | 1:1,000 | Rabbit | Cell Signaling |
| phospho-ERK1/2 | 1:1,000 | Mouse | Upstate |
| ERK1/2 | 1:5,000 | Rabbit | Santa Cruz |
| I-kBα | 1:250 | Rabbit | Abcam |

Nuclear Extracts

Cells were harvested by centrifugation at 300×g for 5 min and lysed in ice-cold cell lysis buffer using an Ultraturrax homogeniser (Janke & Kunke, Germany, 4 strokes of 20 s each, at medium speed). The cell nuclei were pelleted by centrifugation (800×g, 5 min, at 4° C.) and recovered. The pellet was washed twice with ice-cold washing buffer, resuspended in 50 µl ice-cold extraction buffer, and incubated on ice for 30 min. After centrifugation (4000×g, for 10 min, at 4° C.), the supernatant was recovered and the protein concentrations in the nuclear extracts were determined using a commercially available protein assay kit (Bio-Rad Laboratories, UK).

Electromobility Shift Assay

The oligonucleotide containing the NF-κB binding site (upper case), 5'-AgTTgAggggATTTCCCAggC-3' (SEQ ID No. 11) (Santa Cruz Biotechnology) was annealed with a complementary primer and radiolabelled with [$^{32}$P]dCTP (Amersham Pharmacia Biotech, NJ, USA) and electromobility shift assays were performed [as described in (Colli et al., Arterioscler Thromb Vasc Biol. 1997 February; 17(2):265-72)]. Four µg nuclear extracts (see section "Nuclear extracts") were incubated with $1 \times 10^5$ cpm radiolabelled DNA probes for 20 min at room temperature in a final volume of 20 µl binding buffer. Protein-DNA complexes were separated from free DNA probes by electrophoresis through 5% non-denaturing acrylamide gels in 0.5× tris-borate-EDTA buffer (TBE). After running, the gels were dried in a gel dryer (Hoefer Scientific Instruments, NJ, USA) at −80° C. under vacuum for 4 h, and then exposed for 16 h to 40 h to Kodak XAR film at −80° C.

Enzyme-Linked Immunosorbent Assay

Cellular levels of TNFα, IL-1β and TxB-2 were quantified by enzyme-linked immunosorbent assay (ELISA). Conditioned medium from monocytes was sedimented by centrifugation at 300×g at room temperature for 10 min to eliminate cellular debris. Then, the supernatant was recovered and the concentrations of TNFα, IL-1β and TxB-2 were assessed by ELISA, as specified by the manufacturers (Amersham Pharmacia Biotech (NJ, USA).

Drug Treatments

Materials

Pyrrophenone was generously provided by Dr K. Seno (Shionogi Research Laboratories, Shionogi & Co. Ltd., Osaka, Japan) (Ono et al., Biochem J. 2002 May 1; 363(Pt 3):727-35). GPIs were provided by Echelon Biosciences Inc. (UT, USA).

Monocyte Isolation

Human monocytes were obtained from whole blood collected from healthy donors (informed consent was obtained) and anticoagulated with 0.1 vol 3.8% sodium citrate/0.15 mol/l NaCl. The leukocytes were sedimented at 180×g for 15 min at 10° C. The sedimented cells were diluted to the initial volume with citrate-saline and sedimented again. This step was repeated to minimise platelet contamination. The cells were then layered onto Lymphoprep™, and centrifuged at 700×g for 20 min at 20° C. The ring of mononuclear cells was collected and sedimented at 620×g for 7 min at 8° C. The pellet was resuspended in citrate-saline and the cells were washed twice. Monocytes were purified using a discontinuous Percoll™ density gradient; the mononuclear cell preparation was resuspended in RPMI-1640 medium supplemented with 10% heat-inactivated foetal calf serum, and was layered onto a 46% isosmotic Percoll™ solution. After centrifugation at 20° C. for 30 min at 550×g, the cells at the RPMI-1640 medium/Percoll™ interface were collected and sedimented at 620×g. The pellet was resuspended in citrate-saline and the cells were washed twice. The final monocyte preparation was then resuspended in serum-free RPMI-1640 at the concentration required.

The Percoll™ isolated fraction contained approximately 85% monocytes, as assessed by non-specific esterase staining, of which >95% were viable as determined by Trypan-blue staining Pro-Coagualant Activity Assay The pro-coagulant activity of tissue factor (TF activity) was measured in cell lysates according to one-stage clotting time [as reported in (Evangelista et al., Thromb Haemost. 2005; 94, 568-577)]. One hundred µl of cell lysates were added to 100 µl of 37° C. prewarmed normal human plasma. After 30 s, 100 µl 20 mM $CaCl_2$ were added to the mixture and the clotting time was determined using a KC4A Amellung Coagulometer (Mascia Brunelli, Milan, Italy). The data were then converted in arbitrary units by interpolation with a standard curve generated with serial dilutions of human recombinant thromboplastin (Hemoliance, Instrumentation Laboratory).

Results

Figure 2:
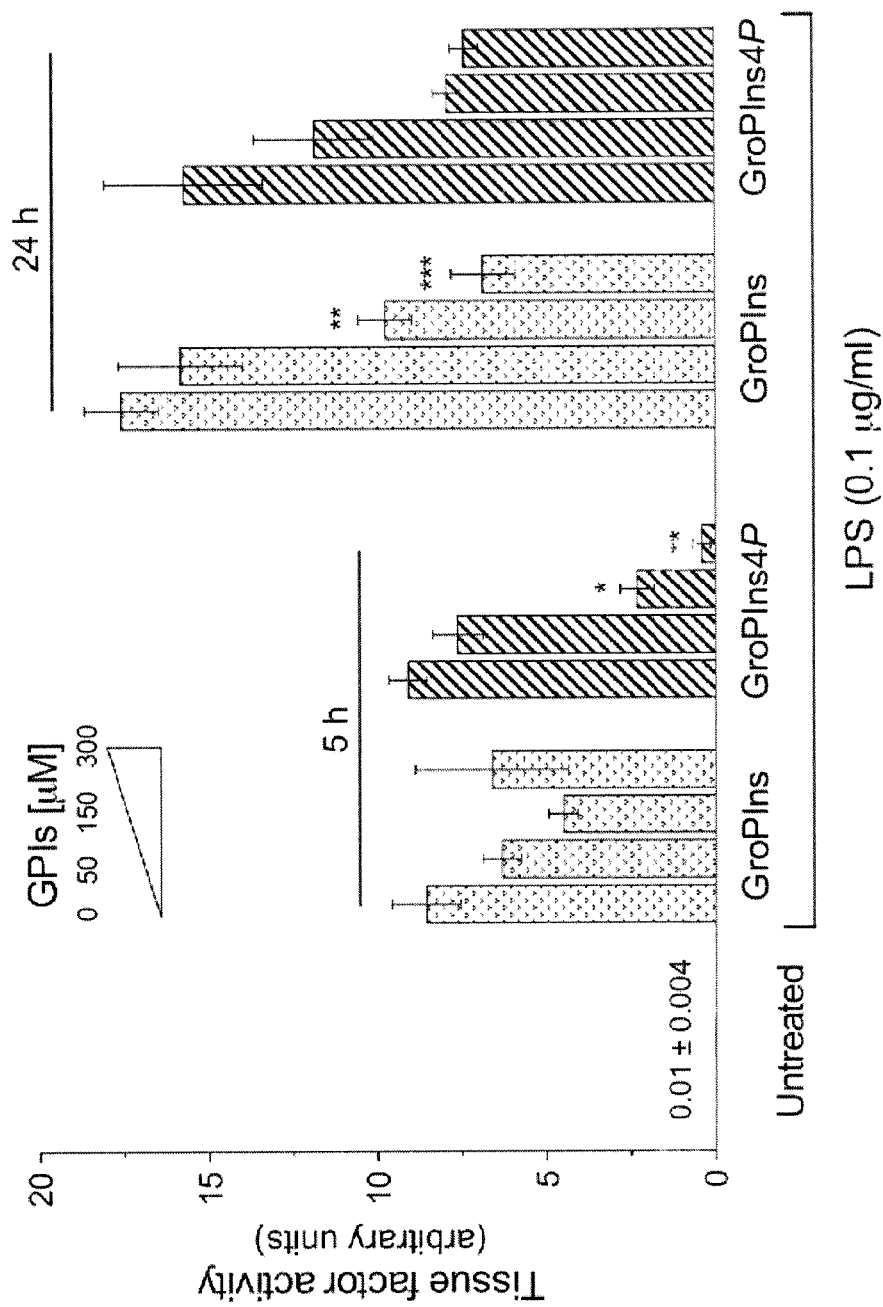
FIG. 2—The glycerophosphoinositols inhibit LPS-activated tissue-factor activity in human monocytes. Human monocytes were purified from peripheral blood of healthy donors and incubated at 37° C. for 20 min without or with different concentrations (from 50 μM to 300 μM) GroPIns or GroPIns4P, and for a further 5 h and 24 h in the absence and in presence of 0.1 μg/ml LPS from E. coli. The data show the pro-coagulant activity of tissue factor, assessed by one-stage clotting time. Data are means (±SD) of three independent experiments performed with cells from different donors. Asterisks indicate statistically significant differences (*p=0.015; p<0.005; *p=0.0003) versus their respective controls. As shown, pro-coagulant activity was not detectable in untreated monocytes, and it was induced in a time-dependent manner by LPS stimulation. Pre-treatment of cells with 50 μM to 300 μM GroPIns or GroPIns4P resulted in a dose-dependent reduction in tissue-factor activity.
Figure 3:
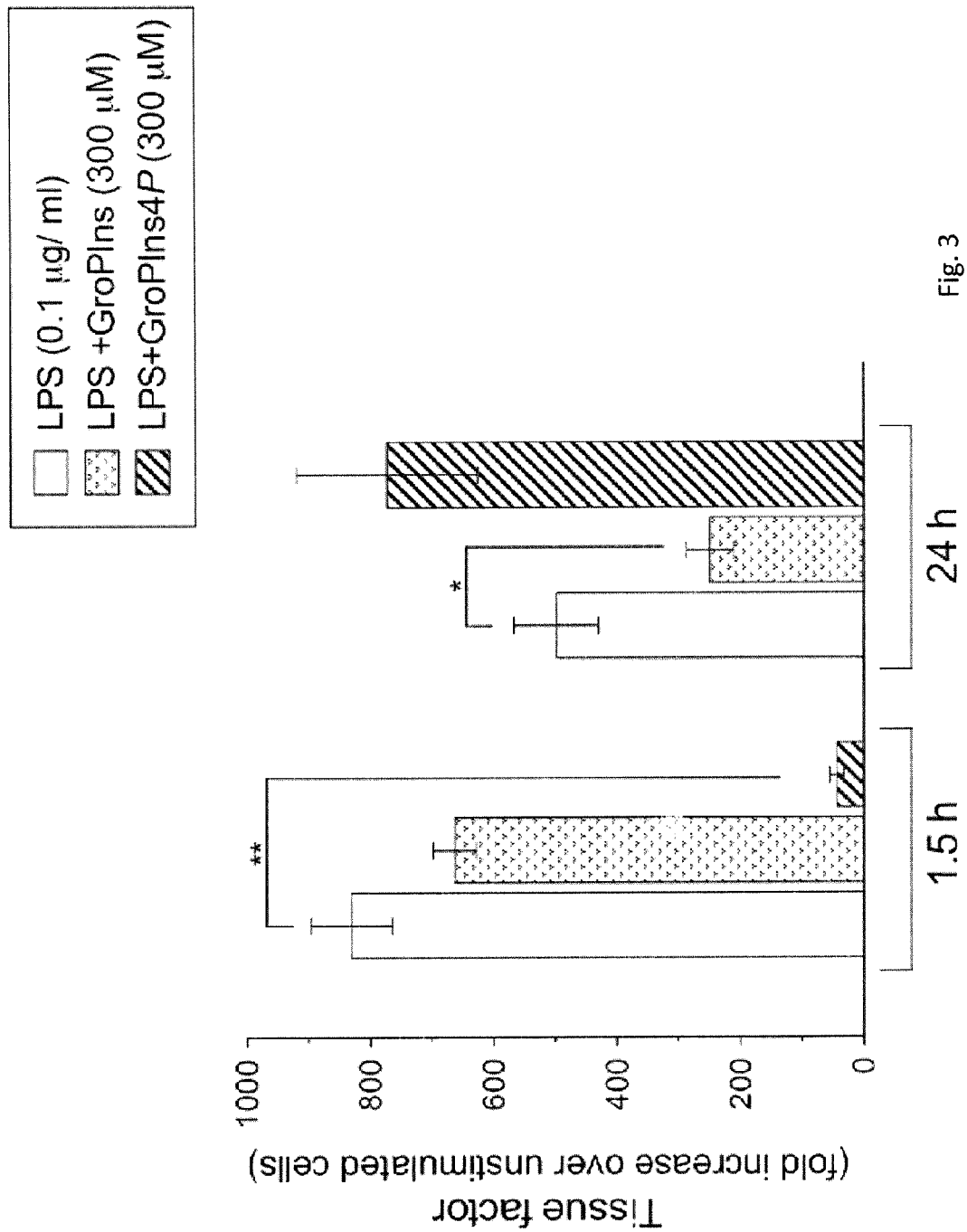
FIG. 3—The glycerophosphoinositols inhibit LPS-induced tissue-factor gene expression. Freshly isolated human monocytes were incubated at 37° C. for 20 min without or with 300 μM GroPIns or GroPIns4P, and for a further 1.5 h or 24 h in the absence and presence of 0.1 μg/ml LPS. At each time point, the total RNA was extracted from cells by the thiocyanate/caesium chloride method and converted to cDNA. Real-time PCR measurements of tissue factor were performed using validated primers. GAPDH served as the house-keeping gene. Each sample was measured in triplicate and the data were calculated with the delta-delta method (2-DDCT) for comparing relative expression data. Monocytes incubated alone for different times were considered the control sample. Measurements of mRNA levels were expressed as fold-increase over control, and are means (±SD) of triplicates from one experiment that is representative of 4 experiments performed with cells from different donors (*p=0.016; **p=0.0052). Treatment of the cells with GroPIns inhibited the transcription levels of tissue factor induced by acute (1.5 h) and chronic (24 h) LPS stimulation, by 15% and 60%, respectively. In contrast, GroPIns4P induced 90% inhibition of LPS-mediated tissue-facor expression at 1.5 h, but was ineffective at 24 h. These results suggested that the glycerophosphoinositols have the same inhibitory effects on LPS-induced tissue-factor gene expression, although they follow different kinetics.

The glycerophosphoinositols inhibit LPS-induced TF activity in human monocytes. TF is a transmembrane glycoprotein that on binding to coagulation factor VII and its active form VIIa, forms the cell-surface complex that is responsible for initiation of the extrinsic pathway of the coagulation cascade, which leads to fibrin clot formation (FIG. 1) (Nemerson, Blood. 1988 January; 71(1):1-8; Suzuki et al., Thromb Res. 2000 May 15; 98(4):269-79). TF is constitutively present on the subendothelial matrix, and it provides the body with a defence mechanism that can stop the loss of blood in the case of tissue injury. Although normally not present on cells in contact with blood, monocytes and vascular endothelial cells can be induced to synthesise and express TF on their membranes by several agonists (including LPS, IL-1, TNFα and C-reactive protein) (Camerer et al., Thromb Res. 1996 Jan. 1; 81(1):1-41; Celi et al., Proc Natl Acad Sci USA. 1994 Sep. 13; 91(19):8767-71; Colucci et al., J Clin Invest. 1983 June; 71(6):1893-6; Semeraro et al., Immunology. 1983 December; 50(4):529-35). Authors investigated the role of the glycerophosphoinositols in the modulation of the LPS-mediated pro-coagulant activity of TF in freshly isolated human monocytes. As shown in FIG. 2, pro-coagulant activity is not detectable in freshly isolated monocytes, although it is induced by acute (5 h) or chronic (24 h) exposure of cells to LPS (0.1 µg/ml at 37° C.). Treatment of monocytes with 50 µM to 300 µM GroPIns or GroPIns4P before LPS stimulation resulted in a dose-dependent reduction in TF activity. Interestingly, although these two glycerophosphoinositols both showed a robust inhibitory effect on LPS-mediated TF activity, their behaviours appeared quite different. Indeed, while the effect of GroPIns is mainly evident at long times (24 h), GroPIns4P showed more rapid kinetics of inhibition, as it was already effective at shorter times (5 h). The results presented above suggest that by reducing the pro-coagulant potential of monocytes, both GroPIns and GroPIns4P would have a protective role against disseminated intravascular coagulation, which is a life-threatening complication of sepsis. To determine whether the inhibitory effects of the glycerophosphoinositols on TF pro-coagulant activity is associated with a reduction in TF gene expression, authors measured the intracellular levels of TF mRNA by reverse-transcriptase PCR (RT-PCR). RNA prepared from untreated cells and from cells treated with LPS in the absence or presence of the glycerophosphoinositols were reverse transcribed and used for parallel assays of TF and GAPDH mRNA by PCR amplification. As expected, no PCR product was detected in control cells (not shown). In contrast, there was strong expression of TF mRNA in cells exposed to LPS (0.1 µg/ml at 37° C. for 1.5 h and 24 h) (FIG. 3). However, treatment of these cells with GroPIns (300 µM) reduced the TF mRNA levels induced by the chronic exposure to LPS (24 h) by about the 60%, whereas no effect was seen with the 1.5-h stimulation with LPS. In contrast, GroPIns4P (300 µM) almost completely blocked (by around 90%) the LPS-mediated TF expression at 1.5 h, but was completely ineffective at 24 h (FIG. 3). Altogether, these data indicate that the glycerophosphoinositols inhibit TF gene expression but, as with the analysis of TF activity, GroPIns and GroPIns4P act with different kinetics.

The glycerophosphoinositols inhibit the LPS-induced expression of the inflammatory cytokines and COX-2.

Figure 4:
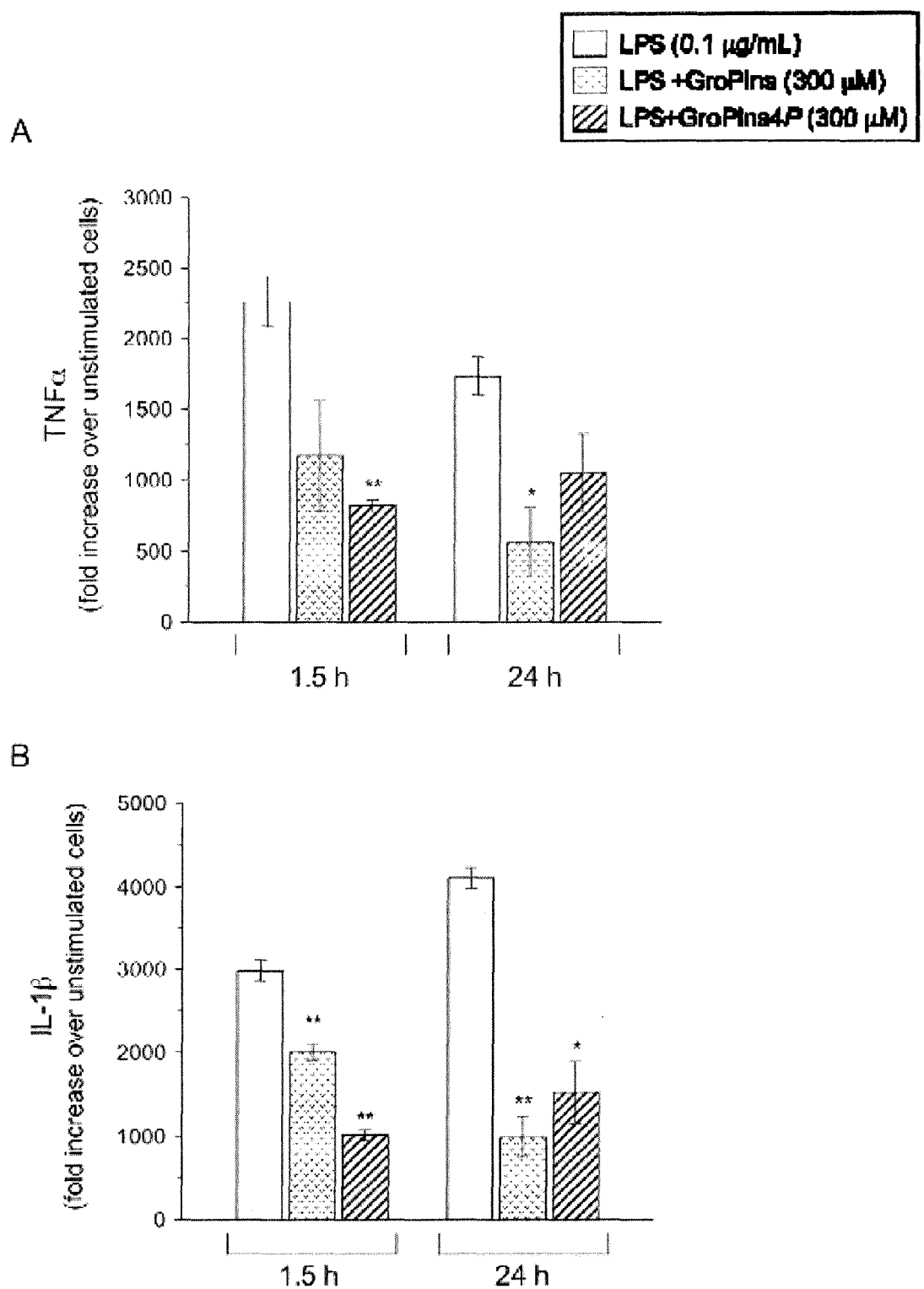
FIG. 4—The glycerophosphoinositols inhibit LPS-mediated gene transcription of TNFα, IL-1β and COX-2. Human monocytes were purified from peripheral blood and incubated at 37° C. for 20 min without or with 300 μM GroPIns or GroPIns4P, and for an additional 1.5 h or 24 h in the absence and presence of 0.1 μg/ml LPS from E. coli. At each time point, RNA was extracted and converted to cDNA for real-time PCR analysis of TNFα, IL-1β and COX-2. Each sample was measured in triplicate and the data were calculated using the delta-delta method (2-DDCT). Transcription of the house-keeping gene GAPDH was used to normalise the data. Measurements of mRNA levels were expressed as fold-increase over the respective control (unstimulated) cells, and are means (±SD) of triplicates from one representative experiment of 4 experiments performed with cells from different donors. Asterisks indicate statistically significant differences (*p<0.0485; **p<0.0092). Treatment of monocytes with GroPIns or GroPIns4P inhibited the effects of LPS on expression of all of the genes analysed, suggesting that glycerophosphoinositols affect a component of the transcription machinery that is common to TNFα, IL-1β, COX-2 and tissue factor.
Figure 4:
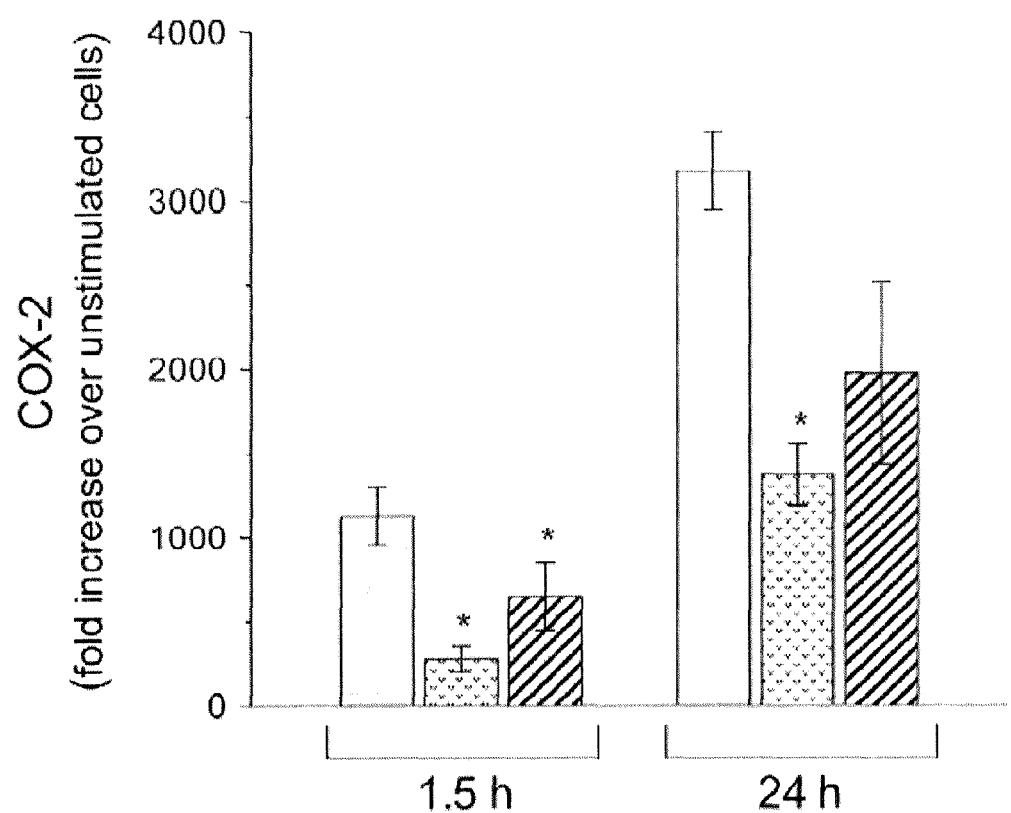
Figure 5:
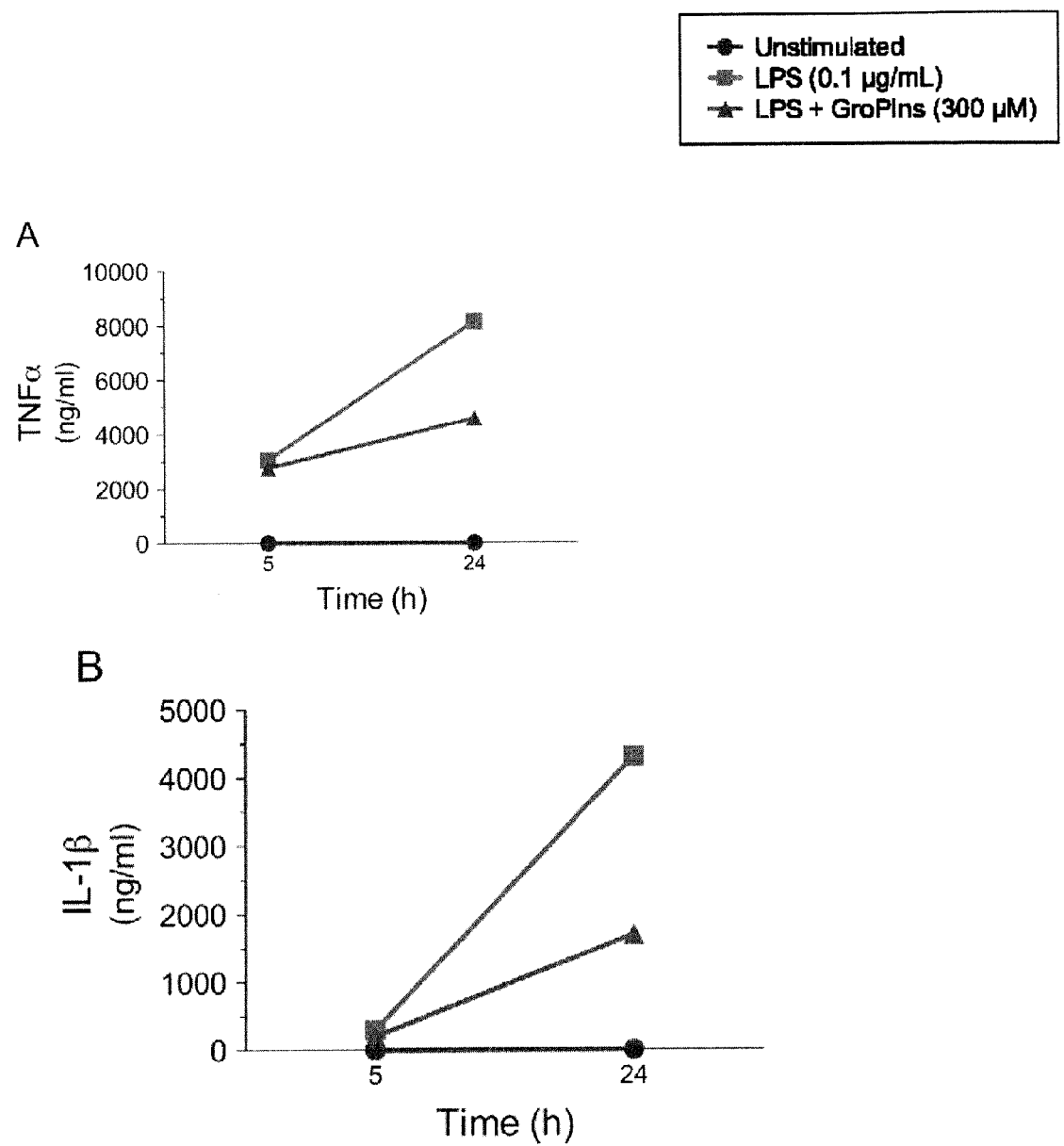
FIG. 5—The inhibitory effects of GroPIns are also evident at the protein expression level. Purified monocytes (4×10³ cells/sample) were pre-incubated for 20 min at 37° C. in the absence and presence of 300 μM GroPIns, and then for a further 5 h and 24 h without or with 0.1 μg/ml LPS from *E. coli*. At the end of this incubation, the levels of TNFα, IL-1β and TxB-2 in the medium were assessed by ELISA. In monocytes alone, the protein concentrations were under the assay detection limits at both the times. The data are representative of three independent experiments performed with cells from different donors. Exposure of monocytes to LPS induced a time-dependent increase in the intracellular levels of all of the cytokines analysed. GroPIns significantly reduced the levels of TNFα, IL-1β and TxB-2 at 24 h, with very small effects at the shorter time, which confirms that GroPIns has a late effect in the inflammatory response induced by LPS in monocytes.
Figure 5:
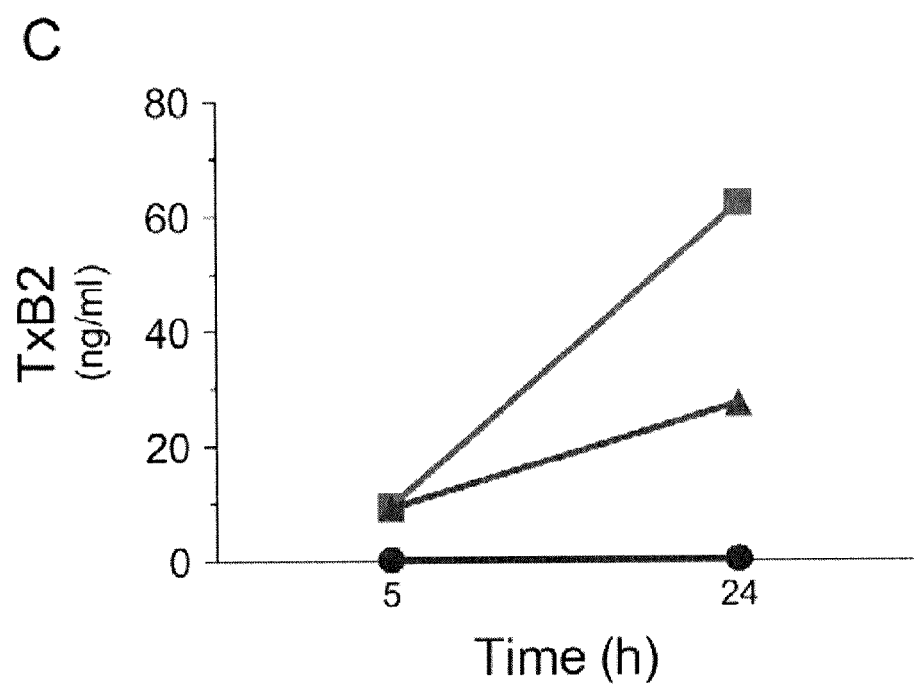

In addition to their roles in initiating the pro-coagulant cascade, monocytes orchestrate the inflammatory response to LPS by expressing a variety of inflammatory cytokines, including COX-2; this in turn produces inflammatory prostanglandins and thromboxane-A2. Thus authors explored the hypothesis that the glycerophosphoinositols can modulate the overall inflammatory responses triggered by LPS in monocytes. To this end, authors have initially analysed the expression profile of a panel of pro-inflammatory genes (COX-2, IL-1β and TNFα), the expression of which is induced by LPS (Suzuki et al., Blood. 2000 Oct. 1; 96(7):2584-91). As shown in FIG. 4, treatment of the cells with the glycerophosphoinositols reduced the effects of LPS stimulation on the expression of all three of these analysed genes. These data also reproduce those of TF (FIG. 3), although with different intensities. In addition to the analysis of the mRNA levels, the inhibitory role of the glycerophosphoinositols on cytokine expression was evaluated, at least for GroPIns, by measuring cytokine released into the supernatant, through specific enzyme-linked immunosorbent assays (ELISAs). As shown in FIG. 5, exposure of monocytes to LPS (0.1 µg/ml) induced an increase in the protein levels between 5 h and 24 h. Interestingly, similar to the effects on gene expression, GroPIns (300 µM) significantly reduced the levels of both IL-1β and TNFα at 24 h, with very low effects at the shorter time. Moreover, at the same time, GroPIns reduced the levels of thromboxane (TxB-2, the stable metabolite of TxA-2). This TxB-2 represents a major product of the metabolic activity of COX-2 in monocytes, which confirms that reduced mRNA expression translates into reduced enzyme activity. From these experiments, it is possible to conclude that both GroPIns and GroPIns4P have a role in the modulation of both pro-inflammatory and pro-thrombotic responses in human monocytes stimulated with LPS. Thus the glycerophosphoinositols can inhibit one or more of the several signalling pathways activated by LPS stimulation.

The glycerophosphoinositols counteract LPS activity by inhibiting NF-κB-mediated gene transcription.

LPS-responsive cis-acting DNA promoter elements have been characterised in the 5'-flanking regions of the TF, COX-2, IL-1β and TNFα genes (Sweet and Hume, 1996). The transcription factors that bind to these LPS response elements include nuclear factor-kB (NF-kB), activator protein-1 (AP-1) and cAMP response element-binding (CREB). These transcription factors collaborate with each other to produce a large number of cytokines, which are barely detectable in resting cells. NF-κB, however, is the only transcription factor required for the induction of all of the LPS-inducible genes so far analysed (Muller et al., Immunobiology. 1993 April; 187 (3-5):233-56).

Figure 6:
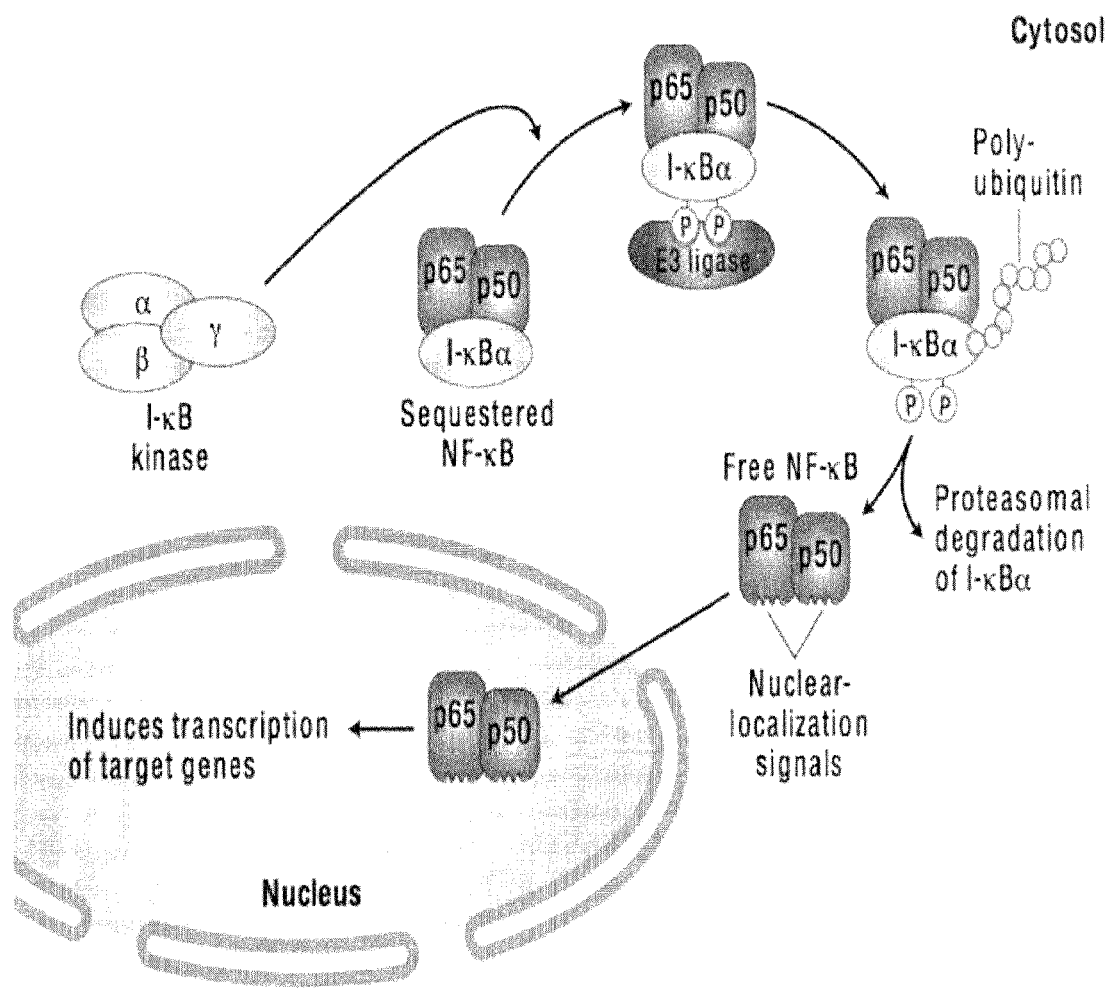
FIG. 6—NF-κB signalling pathway. Scheme showing the mechanisms of NF-κB activation. In resting cells, the dimeric transcription factor NF-κB, which is composed of p50 and/or p65 subunits, is sequestered in the cytosol, bound to the inhibitor I-κBα. Exposure of cells to inflammatory stimuli induces activation of the trimeric I-κB kinase. Following phosphorylation of I-κBα by I-κB kinase and the binding of E3 ubiquitin ligase, polyubiquitination of I-κB targets it for degradation by proteasomes. The removal of I-κBα unmasks the nuclear-localisation signals (NLS) in both of the subunits of NF-κB, allowing their translocation to the nucleus. In the nucleus, NF-κB activates the transcription of numerous target genes, including the gene encoding the α subunit of I-κB, which acts to terminate signalling.

In resting cells, the transcription factor NF-κB is sequestered in the cytosol, bound to the inhibitor I-κB. As schematised in FIG. 6, activation of NF-κB requires rapid serine-specific phosphorylation of the cytoplasmic inhibitory I-κB proteins (Karin, Oncogene. 1999 Nov. 22; 18(49):6867-74). I-κB phosphorylation is followed by its ubiquitination, which targets I-κB for proteasome-mediated degradation (Karin and Ben-Neriah, Annu Rev Immunol. 2000; 18:621-63). Removal of I-κBα, the best characterised NF-κB inhibitor, uncovers the NF-κB nuclear localization signal and allows this transcription factor to migrate into the nucleus, where it induces gene transcription. The converging point of numerous signals that lead to I-κB phosphorylation and consequently to NF-κB activation is the I-κB kinase (IKK) complex. This complex is formed by the regulatory I-κB kinase γ (IKKγ) subunit and two kinase subunits, IKKα and IKKβ (Tak and Firestein, J Clin Invest. 2001 January; 107(1):7-11; Zandi and Karin, Mol Cell Biol. 1999 July; 19(7):4547-51).

Figure 7:
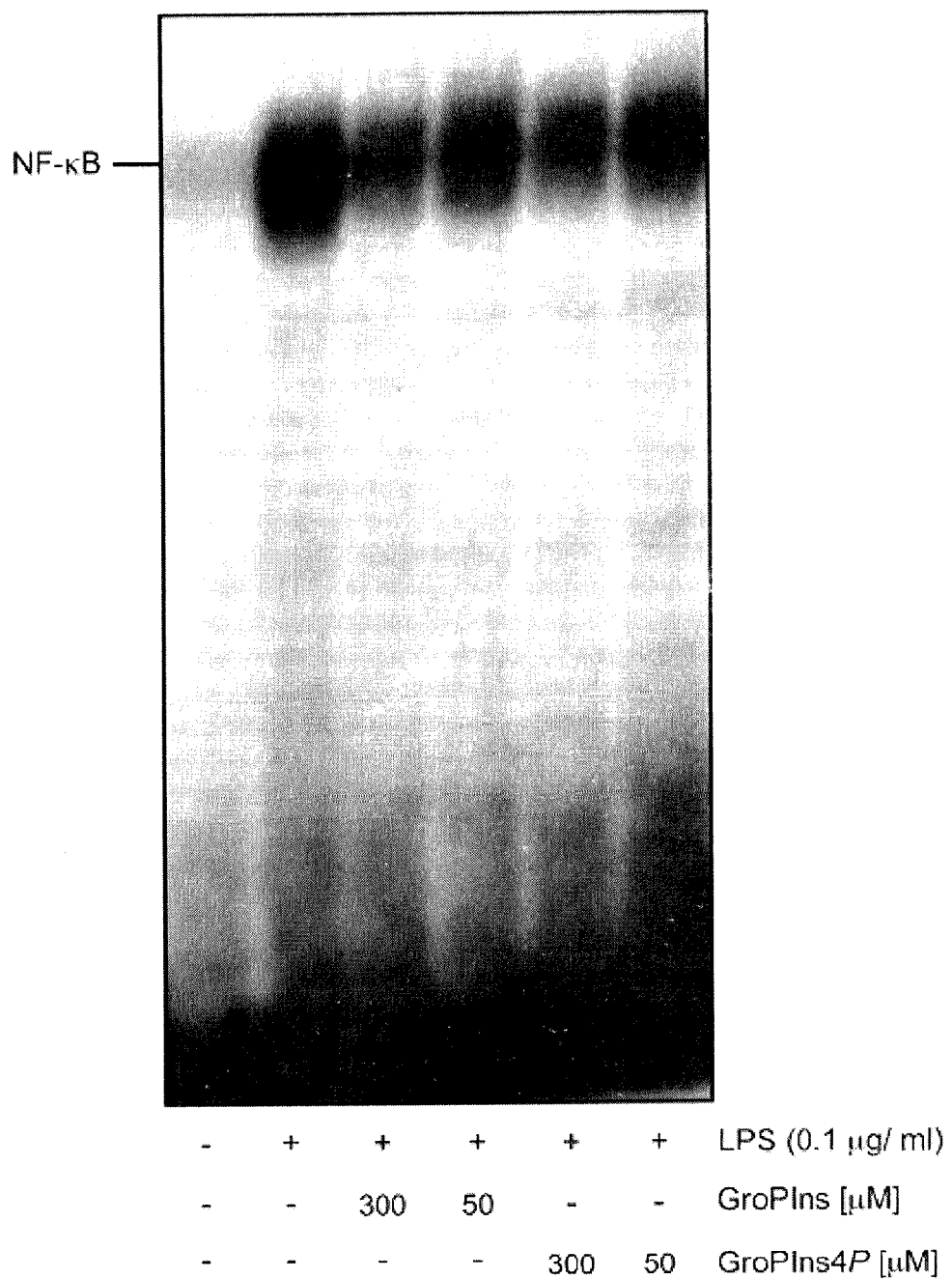
FIG. 7—Glycerophosphoinositols inhibit LPS-stimulated nuclear translocation of NF-κB. Human monocytes purified from the peripheral blood of healthy donors were incubated at 37° C. for 20 min without (−) or with (+) two different concentrations (300 μM and 50 μM) of GroPIns or GroPIns4P, and then for further 1 h in the absence (−) and presence (+) of 0.1 μg/ml LPS from *E. coli*. At the end of the incubation, the cells were lysed and the nuclear extracts were incubated with radiolabelled oligonucleotide probes that contained the NF-κB binding site. Protein-DNA complexes were separated using 6% non-denaturating acrylamide gels and visualised by autoradiography. The results shown are representative of 4 different experiments performed with cells from different donors. The levels of NF-κB in the nucleus were very low in resting cells, and they increased significantly upon LPS stimulation. Pre-treatment with GroPIns or GroPIns4P at 300 μM (but not at 50 μM) reduced NF-κB translocation by about 50%, which indicated that glycerophosphoinositols affects LPS-induced NF-κB activation.
Figure 8:
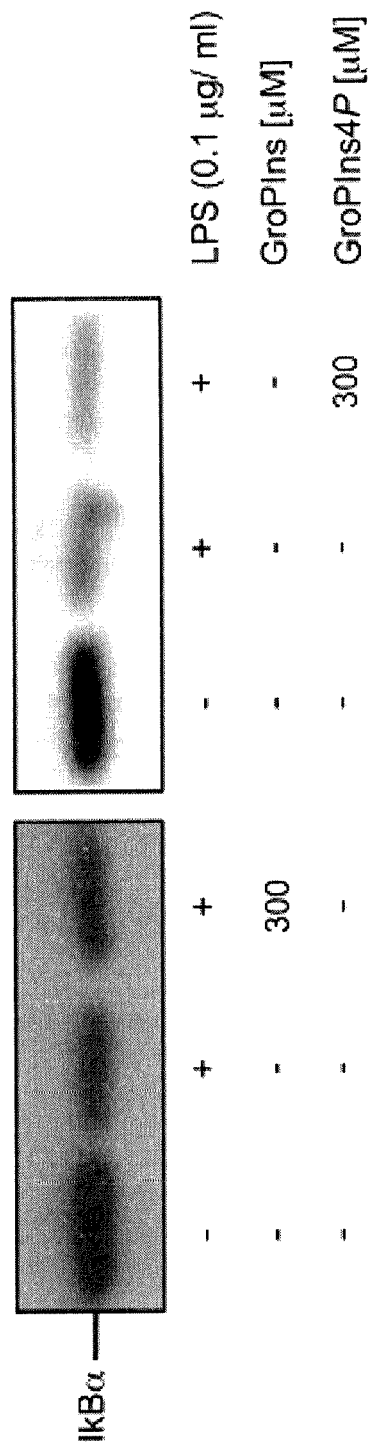
FIG. 8—Glycerophosphoinositols do not affect LPS-induced degradation of I-κBα. Monocytes were incubated at 37° C. for 20 min without or with 300 μM GroPIns or GroPIns4P, and for a further 1 h in the absence and presence of 0.1 μg/ml LPS. After stimulation, the cells were lysed and expression levels of I-κBα were analysed. Proteins were resolved using 10% SDS-PAGE and were probed by Western blotting, using a polyclonal anti-I-κBα antibody. The data are representative of four experiments performed with monocytes isolated from peripheral blood of different donors. Cell exposure to LPS induced degradation of I-κBα both in the absence and presence of the glycerophosphoinositols, indicating that neither GroPIns nor GroPIns4P can modify the cytosolic levels of this NF-κB inhibitor.
Figure 9:
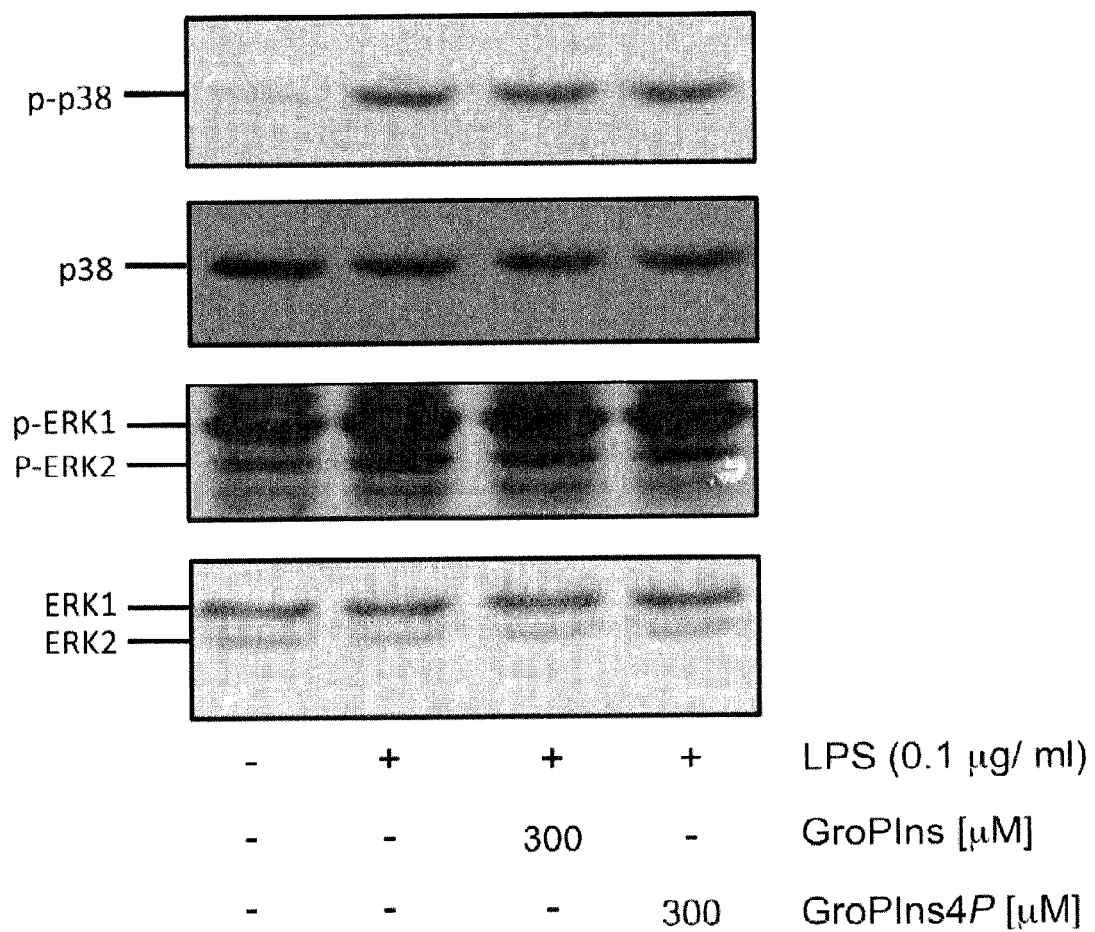
FIG. 9—Glycerophosphoinositols do not affect p38 and ERKs activation levels in monocytes. Monocytes from healthy donors were incubated at 37° C. for 20 min without or with 300 μM GroPIns or GroPIns4P, and for 0.1 μg/ml LPS from *E. coli*. in the absence and presence of 0.1 μg/ml LPS from *E. coli*. Resentative Western blots are shown, as resolved using 10% SDS-PAGE, showing phosphorylated (p-) and total levels of p38 and ERK1/2. All of the blots were representative of at least three independent experiments. Treatment of these monocytes with GroPIns or GroPIns4P did not affect the phosphorylation levels of p38 and ERK1/2, which indicated that the glycerophosphoinositols do not modulate the activities of these kinases.

To determine whether the glycerophosphoinositols treatments affected LPS-mediated gene expression by preventing the activation of NF-κB, nuclear extracts were prepared from monocytes exposed to LPS (0.1 µg/ml at 37° C.) in the absence and presence of GroPIns and GroPIns4P; these were then analysed by electrophoretic mobility shift assays (EMSAs). Nuclear localisation of NF-κB was induced within 1 h of LPS stimulation, and both GroPIns and GroPIns4P (both at 300 µM) reduced the amount of nuclear NF-κB by about the 50% (FIG. 7). To define the mechanism through which the glycerophosphoinositols might affect this NF-κB activity, authors also used Western blotting to measure the cytosolic levels of I-κBα (which binds to NF-κB and inhibits its nuclear translocation). As shown in FIG. 8, LPS stimulation (0.1 µg/ml for 1 h) induced the degradation of I-κBα. However, treatment of these cells with GroPIns or GroPIns4P (both at 300 µM) did not affect this LPS activity, which indicates that the glycerophosphoinositols act on NF-κB independent from I-κBα. Additional mechanisms that control the transcriptional activity of NF-κB include post-translational modifications, such as phosphorylation and acetylation (Ashburner et al., Mol Cell Biol. 2001 October; 21(20):7065-77; Madrid et al., J Biol Chem. 2001 Jun. 1; 276(22):18934-40; Sizemore et al., Mol Cell Biol. 1999 July; 19(7):4798-80). Several kinases have been postulated to phosphorylate NF-κB, including the stress kinase p38 and the MAP kinases ERK1/2 (Kim et al., Chem Biol Interact. 2008 Jan. 30; 171 (2):133-41). To complete our analysis of the mechanisms of action of the glycerophosphoinositols, the phosphorylation levels of p38 and ERK1/2 were monitored by Western blotting. The data reported in FIG. 9 indicate that in this cell system, LPS activates p38 (but not ERK1/2), and treatment with GroPIns or GroPIns4P (both at 300 µM) is completely ineffective. The experiments presented in this section demonstrate that GroPIns and GroPIns4P do not affect the pathways upstream NF-κB, the inhibition of which is probably due to a direct effect of the glycerophosphoinositols on NF-κB. On the other hand, it cannot be excluded that different experimental conditions could reveal effects even upstream of NF-κB.

Figure 10:
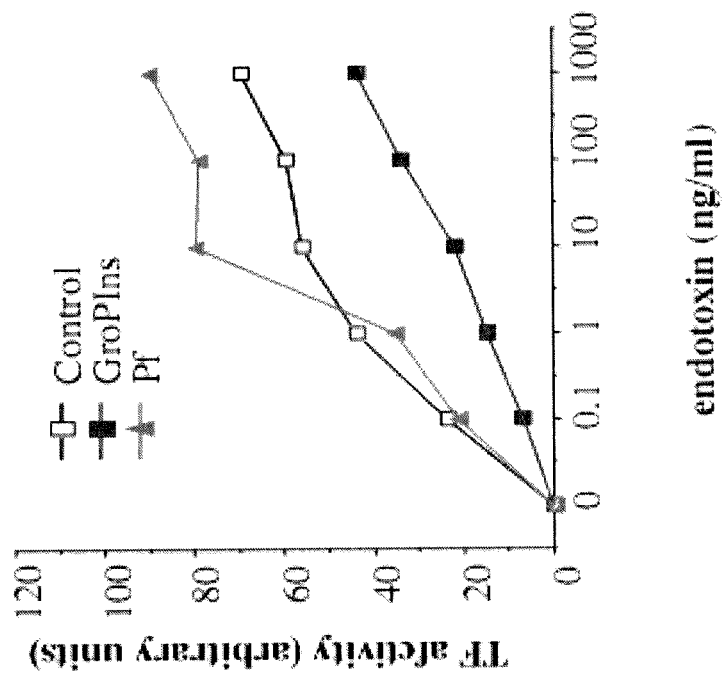
FIG. 10—GroPIns (300 μM), but not pyrrofenone, reduces TF activity in human monocytes activated by different concentrations of endotoxin for 24 hours. The glycerophosphoinositol, differently from the $PLA_2IV\alpha$ inhibitor, inhibits LPS-activated tissue-factor activity in human monocytes. Human monocytes were purified from peripheral blood of two healthy donors (experiment I and II) and pre-incubated at 37° C. for 20 min without (black line) or with 300 μM glycerophosphoinositol (GroPIns, blue line) or 0.5 μM $PLA_2IV\alpha$ inhibitor (pyrrophenone, Pf, red line), and for a further 24 h in the absence or presence of increasing concentrations of LPS from *E. coli* (endotoxin). The data show the pro-coagulant activity of tissue factor, assessed by one-stage clotting time, expressed as arbitrary units.
Figure 10:
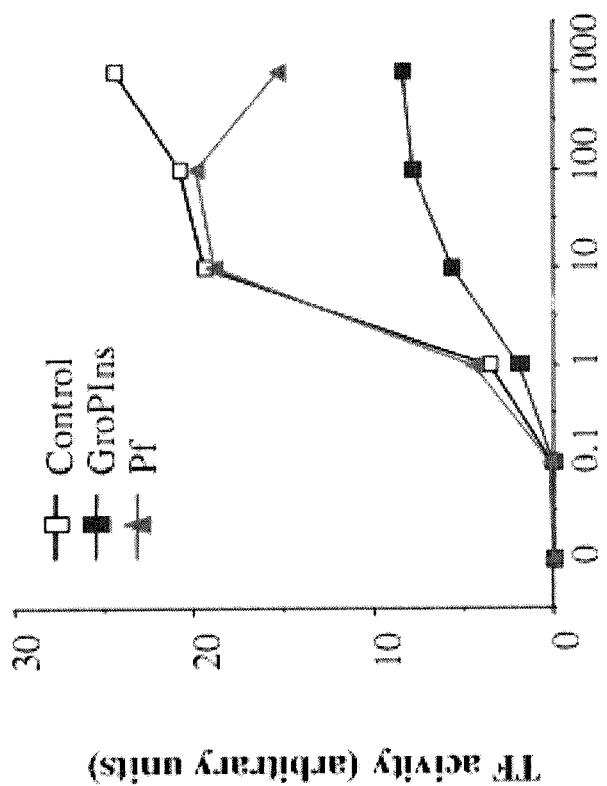
Figure 11:
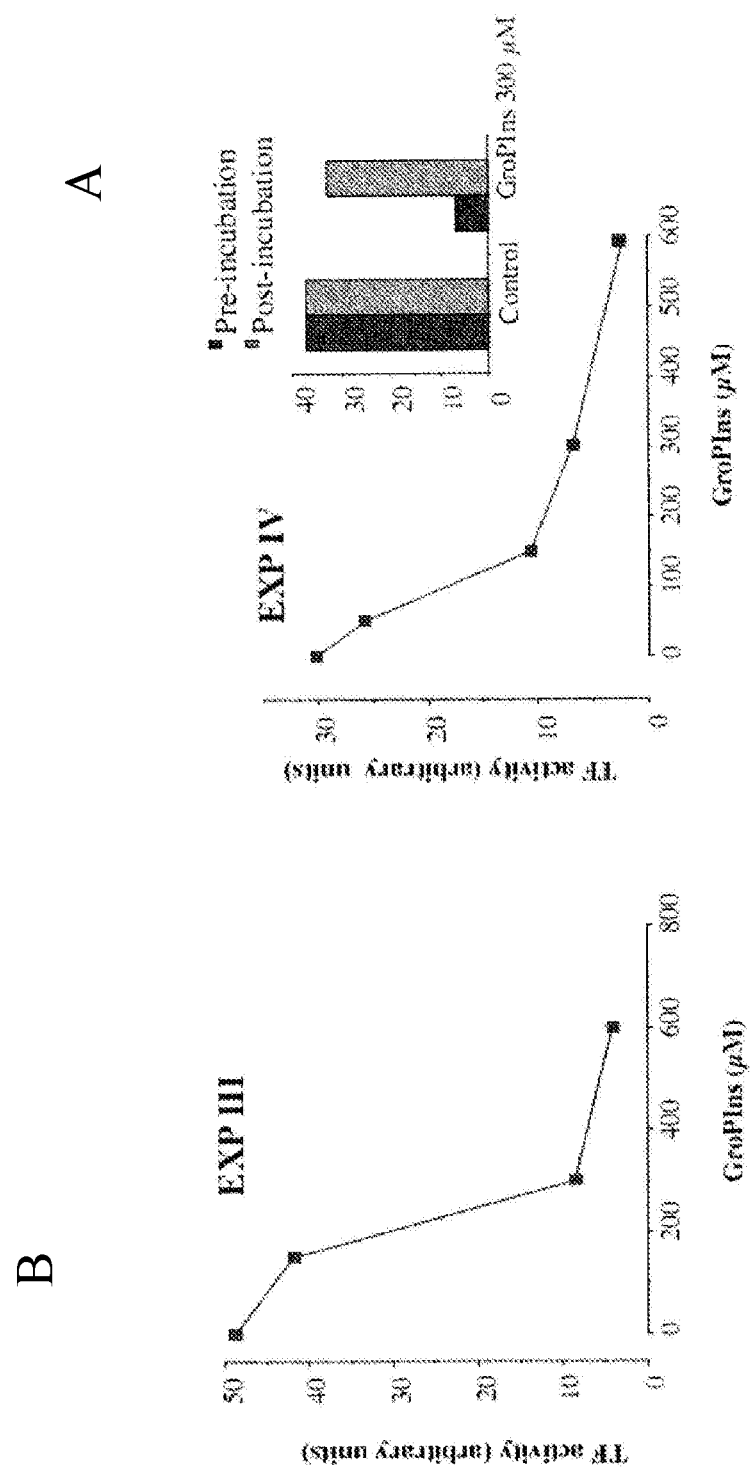
FIG. 11—GroPIns dose-dependently reduces TF activity in monocytes activated by endotoxin (10 ng/ml) for 24 hours. The glycerophosphoinositol inhibits in a dose-dependent manner LPS-activated tissue-factor activity in human monocytes. Human monocytes were purified from peripheral blood of three healthy donors (experiments III, IV and V) and pre-incubated at 37° C. for 20 min without or with increasing concentrations of glycerophosphoinositol (GroPIns) and for a further 24 h in the absence or presence of 10 ng/ml of LPS from *E. coli* (endotoxin). The data show the pro-coagulant activity of tissue factor, assessed by one-stage clotting time, expressed as arbitrary units. The two insets in Exp IV and V show the pro-coagulant activity of tissue factor, assessed in cells stimulated by 10 ng/ml of endotoxin, with (filled bars) or without (dotted bars) 20 min pre-incubation at 37° C., in absence (Control) or in presence of 300 μM GroPIns.
Figure 11:
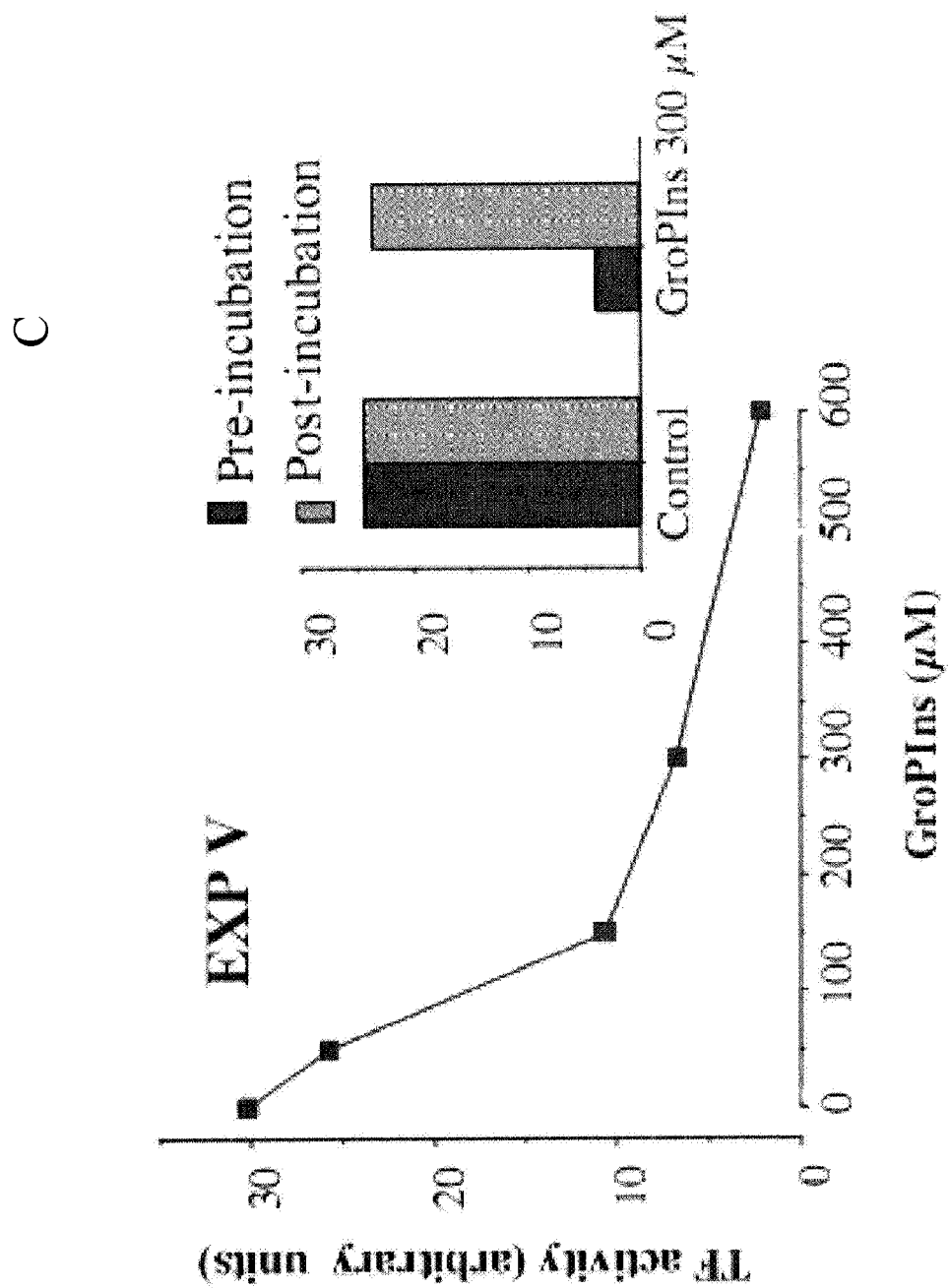
Figure 12:
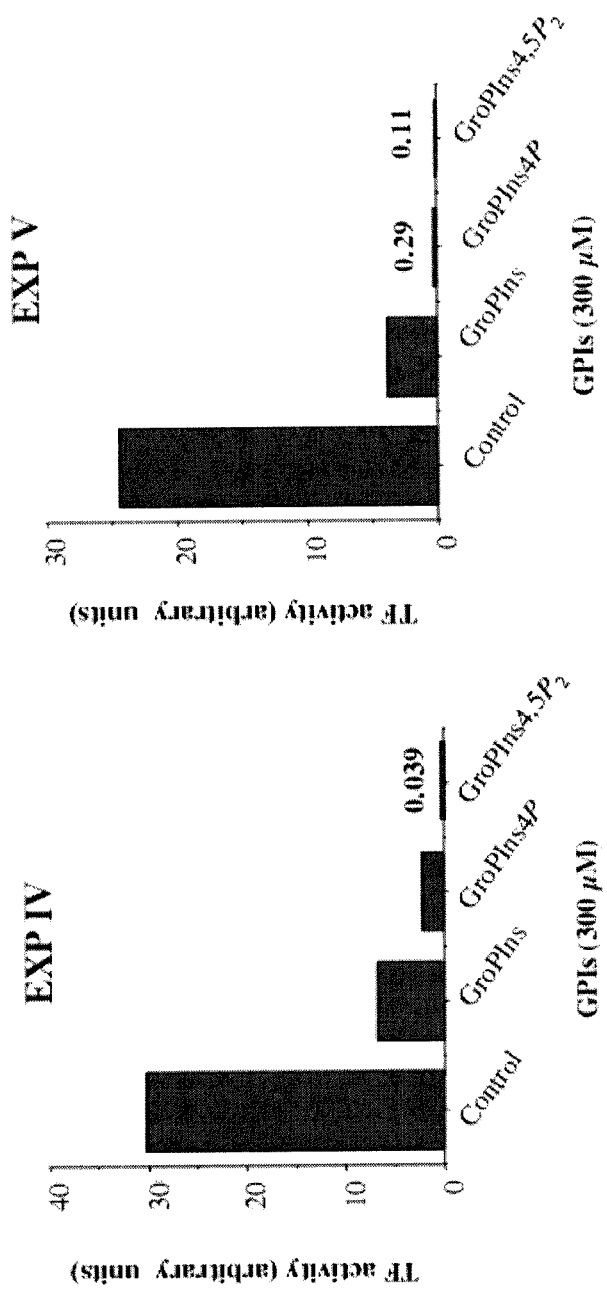
FIG. 12—Not only GroPIns but also GroPIns4P and $GroPIns4,5P_2$ (apparenity with higher efficacy than GroPIns) reduce TF activity in monocytes activated by endotoxin (10 ng/ml) for 24 hours. The glycerophosphoinositols inhibit LPS-activated tissue-factor activity in human monocytes. Human monocytes were purified from peripheral blood of two healthy donors (experiment IV and V) and pre-incubated at 37° C. for 20 min without (Control) or with 300 μM glycerophosphoinositols (GroPIns, GroPIns4P or $GroPIns4,5P_2$ and for a further 24 h in the presence of 10 ng/ml of LPS from *E. coli* (endotoxin). The data show the pro-coagulant activity of tissue factor, assessed by one-stage clotting time, expressed as arbitrary units.

It has also been demonstrated the role of the glycerophosphoinositols in the inhibition of the LPS-induced pro-coagulant activity of tissue factor in freshly isolated human monocytes. As shown in FIGS. 10-12, pro-coagulant activity is not detectable in freshly isolated monocytes, although it is strongly induced by exposure of cells to LPS. Treatment of monocytes with GPI, before LPS stimulation, resulted in a dose-dependent reduction in tissue-factor activity. Also the other glycerophosphoinositol derivatives, the GroPIns4P and GroPIns4,5$P_2$, are able to inhibit LPS-induced pro-coagulant activity of tissue factor, and they seem more potent than the GroPIns.

Interestingly, the effect of these glycerophosphoinositols appeared quite different from the PLA$_2$IVα inhibitor, pyrrophenone. Indeed, the pre-treatment of monocytes with pyrrophenone, at a concentration able to completely abolish PLA$_2$IVα activity in these cells, does not significantly inhibit endotoxin effect on tissue-factor activity.

Altogether these data show a different anti-inflammatory mechanism of action and therapeutic applications in all of pathologies where an inhibition of endotoxin effects is needed, of glycerophosinositols from classical blockers of the arachidonate pathway.

Example 2

Materials

Glycerophosphoinositol was provided by EUTICALS s.p.a. Lipopolysaccharide (from *E. Coli*) was from Sigma-Aldrich. Human recombinant chemokine C-C motif ligand 2 (CCL2) and cytokines tumor necrosis factor α (TNFα), interferon γ (IFN-γ), interleukin 10 (IL-10) and transforming growth factor β1 (TGFβ1) were from R&D System.

Monocytes Isolation from Peripheral Blood and In Vitro Activation

Freshly isolated human monocytes, which have been used for all the above-mentioned experiments, were purified from buffy coat prepared at I.N.T. Pascale in Naples. Monocytes were obtained by gradient density centrifugation with Ficoll Paque PLUS (GE Healthcare) and subsequent positive separation with Monocytes isolation kit (Miltenyi). In detail, buffy coat from healthy donor was diluted with phosphate buffered saline (PBS), layered on Ficoll Paque PLUS and centrifuged at 400×g for 30 minutes at room temperature. The ring of peripheral blood mononuclear cells (PMBC) was collected, washed twice, in order to remove platelets, incubated with anti-human CD14 microbeads (Miltenyi) which specifically bind to monocytes, and magnetically separated on column (Miltenyi). The viability of cells was determined by trypan blue staining. The purity of isolated cells (98%) was microscopically detected after centrifugation and staining with modified Wright-Giemsa dye (Diff Quick, Medion Diagnostic AG).

Monocytes were plated at a density of 5×10$^6$ cells/well in six-well culture plate in RPMI 1640 medium (Gibco) supplemented with 5% heat-inactivated human AB serum (Sigma-Aldrich) and 1% streptomycin and penicillin. In order to mimic the microenvironmental changes and the timing of human host response covering the different phases of the inflammatory reaction cultured cells have been exposed to sequential changes of microenvironmental conditions: after plating, freshly isolated human monocytes were exposed to CCL2 (20 ng/ml) at 37° C. After 2 hours CCL2 was removed, cells were washed and fresh medium containing LPS (5 ng/ml) was added. During the treatment, the temperature was increased at 39° C. After 3 hours and 7 hours respectively, TNFα (10 ng/ml) and IFNγ (25 ng/ml) were added. Temperature was maintained at 39° C. until 14 hours, when all inflammatory stimuli were removed, monocytes were washed and fresh medium containing IL-10 (20 ng/ml) was added. The temperature was shifted back to 37° C. until the end of the experiment. At 24 hours medium containing IL-10 was removed, fresh medium containing TGFβ (10 ng/ml) was added and the culture prolonged until 48 h. Samples (both total RNA and supernatants) were collected at time 0 h, 4 h, 14 h, 24 h, 48 h. Freshly isolated human monocytes were considered as control samples at time 0 h.

Total RNA Purification, Reverse Transcription, Real-Time PCR Reaction and Data Analysis.

Total RNA was extracted with RNeasy kit (Qiagen) according to the manufacturer's instructions. Both integrity and quality of total RNA were checked by agarose gel electrophoresis and the concentration of each RNA sample was assessed spectrophotometrically. Total RNAs were reverse-transcribed to cDNA (QuantiTect Reverse Transcription kit, Qiagen) with oligo-dT and random primers, according to manufacturer's protocol. Then, 20 μL of a mix containing cDNA, 500 nM primers and SYBR Green master mix (Roche) was used for a real time PCR reaction performed using Light Cycler 480 Instrument II (Roche). Each cDNA sample was measured in triplicate. Relative gene expression values were calculated using the efficiency correction method (Pfaffl method), which calculate the relative expression ratio from real time PCR efficiency and the CT value between the target gene and the reference one, relative to calibrator sample, i.e. time 0 h. (Pfaffl, Nucleic Acids Research, 2001, May 1; 29(9):e45). Hypoxanthine-guanine phosphoribosyl-transferase (HPRT) was used as reference gene.

Primers: COX-2-F: TCCAAACACAGTGCACTACA (SEQ ID No. 12); COX-2-R: GGTGGACTGTCAAT-CAAATG (SEQ ID No. 13); PLA$_2$IVα-F: TTTACGG-TAGTGGTGTTACG (SEQ ID No. 14); PLA$_2$IVα-R: CTGT-CAGGGGTTGTAGAGAT (SEQ ID No. 15); IκBα-F: AAGGCTACCAACTACAATGG (SEQ ID No. 16); IκBα-R: TGAGCATTGACATCAGCAC (SEQ ID No. 17); IL-1β-F: GATGCACCTGTACGATCACT (SEQ ID No. 18); IL-1β-R: GACATGGAGAACACCACTTG (SEQ ID No. 19); IL-1Rα-F: GAGGAGGAGAAGGTGAAGAC (SEQ ID No. 20); IL-1Rα-R: CTTCTGGTTAACATCCCAGA (SEQ ID No. 21). Primer sequences for IL-1RII and HPRT were supplied by Qiagen.

Protein Detection by ELISA

Extracellular levels of IL-1β, TNFα and IL-6 were measured by enzyme-linked immunosorbent assay (ELISA) from R&D System. Supernatants collected at time 0 h, 4 h, 14 h, 24 h, 48 h were sedimented by centrifugation at 5000 rpm for 5 minutes to eliminate cellular debris. Then the recovered supernatants were loaded onto plates according to manufacturer's protocol and the concentration of the protein was assessed spectrophotometrically.

Results

Inflammation is a beneficial host response to foreign challenge or tissue injury that leads ultimately to the restoration of tissue structure and function. Innate and adaptive immune cells are the two integral components of the host's defense system providing the appropriate signals for instructing each other to release the appropriate effectors to mount and cease a proper inflammatory response. A prolonged or uncontrolled inflammation can indeed lead to the pathogenesis of many disease states. As prolonged activation of immune system cells is the driving force behind inflammatory diseases, the identification of anti-inflammatory compounds able to switch off the pro-inflammatory response and restore the immunological homeostasis seems to be crucial. Results obtained unveiled a new function of glycerophosphoinositols as endogenous anti-inflammatory compounds; in particular glycerophosphoinositol was found to be particularly effective in the inhibition of lipopolysaccharide-induced pro-coagulant activity of tissue factor in primary human monocytes.

Figure 13:
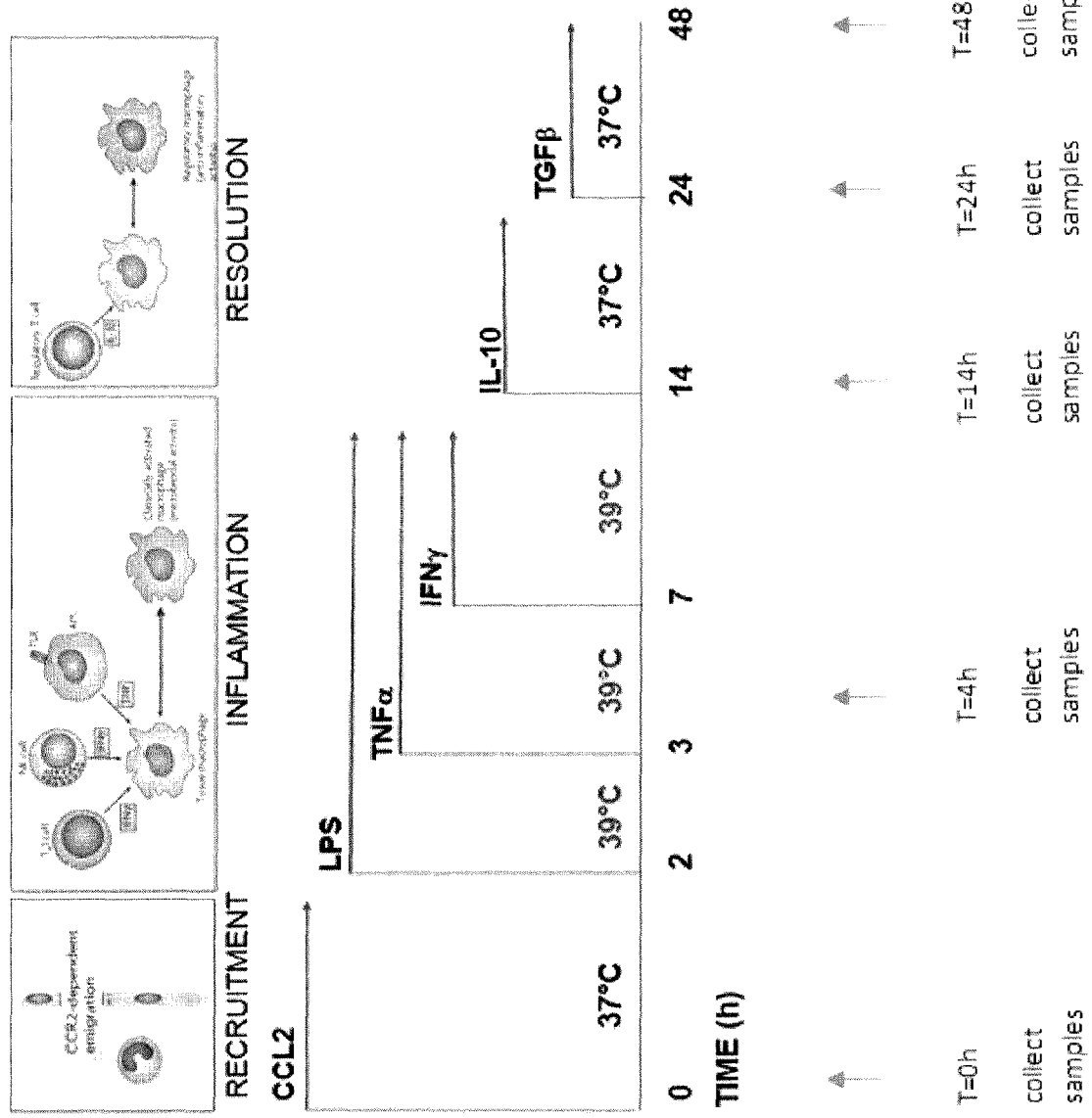
FIG. 13—The in vitro model of human innate immunity inflammation. Schematic representation and timing of the in vitro stimulation of human monocytes. In order to mimic the microenvironmental changes and the timing of human host response that covers the different phases of the inflammatory reaction, from recruitment and onset, to development and resolution of inflammation, cultured cells have been exposed to sequential changes of microenvironmental conditions. Monocytes in culture were exposed to chemokine C-C motif ligand 2 (CCL2), responsible for monocytes recruitment to sites of injury through endothelial cells adhesion, lipopolysaccharide (LPS), as a pathogen insult, tumor necrosis factor α (TNFα) and interferon γ (IFN-γ) as inducers of acute phase of inflammation and finally with interleukin 10 (IL-10) and transforming growth factor β (TGF-β), responsible for the resolution of inflammation. In detail: at time zero freshly isolated human monocytes were exposed to CCL2 (20 ng/ml) at 37° C. After 2 hours CCL2 was removed, cells were washed and fresh medium containing LPS (5 ng/ml) was added. During the treatment, the temperature was increased at 39° C. After 3 hours and 7 hours, respectively, TNFα (10 ng/ml) and IFNγ (25 ng/ml) were added. Temperature was maintained at 39° C. until 14 hours when all inflammatory stimuli were removed, monocytes were washed and fresh medium containing IL-10 (20 ng/ml) was added. The temperature was shifted back to 37° C. until the end of the experiment. At 24 hours medium containing IL-10 was removed, fresh medium containing TGFβ (10 ng/ml) was added and the culture prolonged until 48 h. Samples were collected at time 0 h, 4 h, 14 h, 24 h, 48 h. Freshly isolated human monocytes were considered as control samples at time 0 h.

Authors' further investigations reinforced the observation about glycerophosphoinositols as endogenous metabolites which exert an anti-inflammatory function in innate immunity cells. In detail, the role of glycerophosphoinositol has been evaluated in a complete in vitro model of human innate immunity inflammation (FIG. 13). The need for a new and specific human model of inflammation comes from the absence of a comprehensive model of the human inflammatory response that covers the different phases of the inflammatory reaction, from recruitment and onset, to development and resolution of inflammation, ending up with the re-establishment of homeostasis. The model is based on human primary blood monocytes, which are key players in both initiation and resolution of inflammation due to their ability to adopt different phenotypes according to changes in the tissue microenvironment. In order to imitate the microenvironmental changes and the timing of host response, cultured cells have been exposed to sequential changes of microenvironmental conditions (chemokines and cytokines, temperature) for 48 hours. Samples have been collected after 4, 14, 24, 48 hours, corresponding to onset of inflammation, full inflammation and resolution. Cultured monocytes have been sequentially treated with chemokine C-C motif ligand 2 (CCL2), responsible for monocytes recruitment to sites of injury through endothelial cells adhesion, lipopolysaccharide (LPS), as a pathogen insult, tumor necrosis factor α (TNFα) and interferon γ (IFN-γ) as inducers of acute phase of inflammation and finally with interleukin 10 (IL-10) and transforming growth factor β (TGF-β), responsible for the resolution of inflammation.

Preliminary experiments have been performed to evaluate the activity of glycerophosphoinositol in the model of inflammation described above. Human monocytes were purified from healthy donors and treated according to the in vitro model of human inflammation, previously described, with or without 300 μM glycerophosphoinositol during the inflammatory process. In detail glycerophosphoinositol was added to cells in culture 20 minutes before LPS, IL-10 and TGF-β treatment, that is, again after each wash. Preliminary results from these experiments have shown that exogenously added glycerophosphoinositol affected the onset of inflammation.

Figure 14:
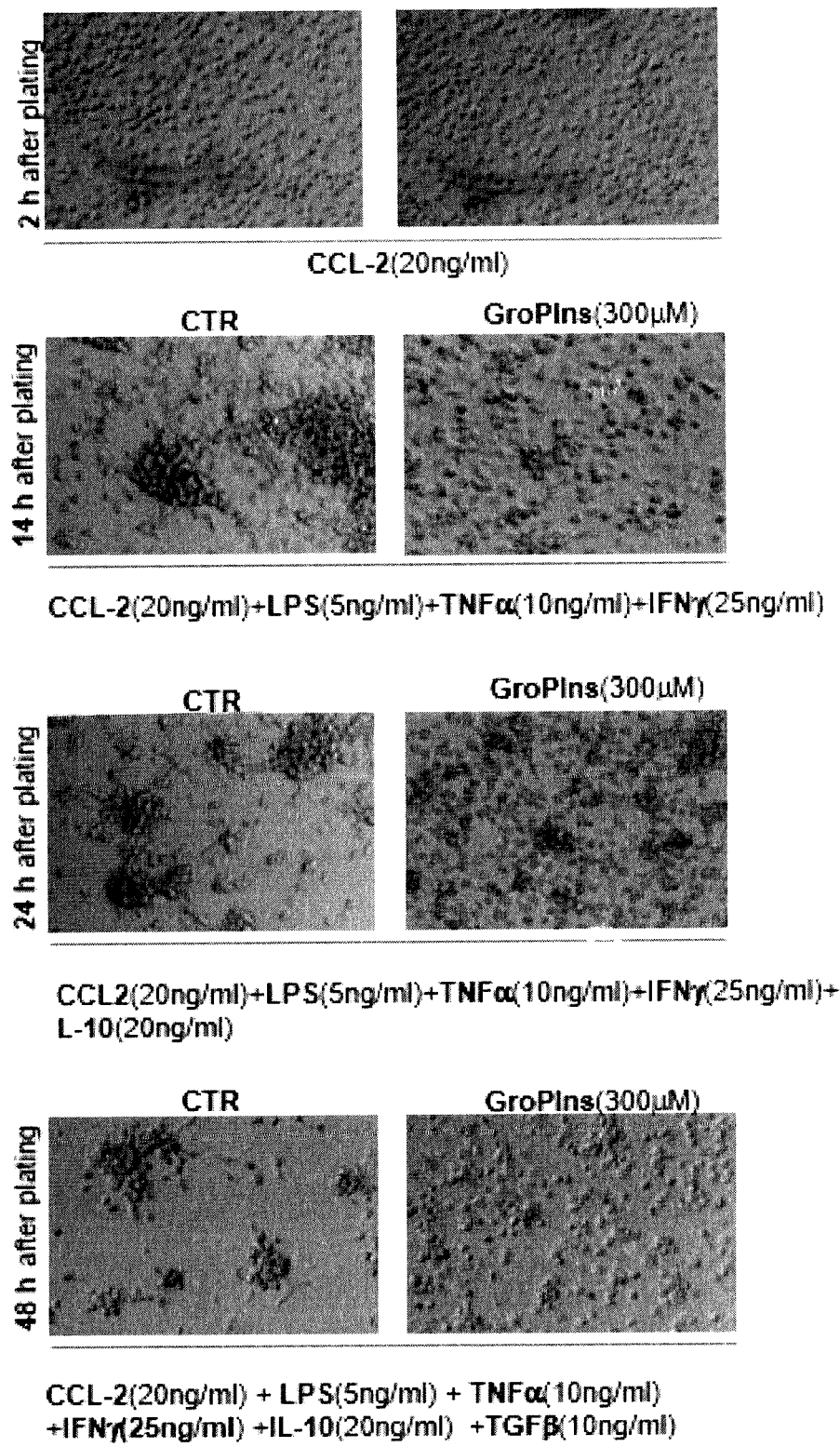
FIG. 14—Glycerophosphoinositol affects the morphological features of cultured monocytes. Human monocytes purified from one donor were treated according to the in vitro model of human inflammation, previously described, in absence (left panel, ctr) or in presence (right panel, GroPins) of 300 μM glycerophosphoinositol. In detail, glycerophosphoinositol was added to cells in culture 20 minutes before LPS, IL-10 and TGF-β treatment, that is, again after each wash. Images were acquired at time 2 h, 14 h, 24 h, 48 h by light microscopy. Upon exposure to LPS, TNFα and IFN-γ human monocytes become activated in inflammatory macrophages, release proinflammatory cytokines and undergo inflammation-induced death (pyroptosis). Interestingly the exposure of cells to glycerophosphoinositol during the inflammatory process decreased the inflammatory phenotype and exerted a protective function; indeed in presence of glycerophosphoinositol the cellular viability increased.
Figure 15:
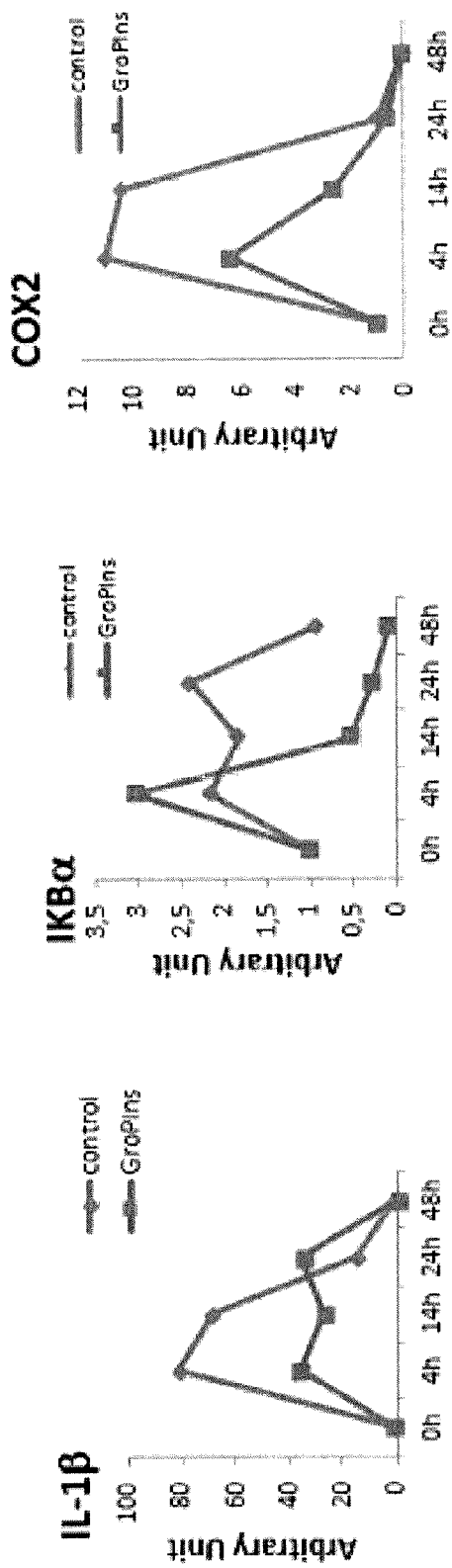
FIG. 15—Glycerophosphoinositol modulates the kinetic transcriptional profile of genes involved in the regulation of inflammatory response. Human monocytes were purified from one donor and treated according to the in vitro model of human inflammation, previously described, in absence (blue line) or in presence (red line) of 300 μM glycerophosphoinositol. In detail glycerophosphoinositol was added to cells in culture 20 minutes before LPS, IL-10 and TGF-β, that is, again after each wash. Samples were collected at time 4 h, 14 h, 24 h, 48 h; freshly isolated monocytes have been considered as control at time 0 h. Total RNA was extracted from cells by RNeasy kit (Qiagen) and reverse-transcribed to cDNA (QuantiTect Reverse Transcription kit, Qiagen). Real-time PCR analysis of the following genes: interleukin 1β (IL-1β), inhibitor of κB, α (IκB-α), cyclooxygenase 2 (COX-2) phospholipase $A_2IV\alpha$ ($PLA_2IV\alpha$), Interleukin-1 receptor α (IL-1Rα), interleukin-1 receptor II (IL-1RII) was performed using validated primers and HPRT gene was used as reference. Each sample was measured in triplicate and data were analyzed with Pfaffl methods for comparing relative expression data. The measurement of mRNA expression was expressed as fold-increase over control (time 0 h). Glycerophosphoinositol affected the expression of the genes analysed: in particular it hampered the expression of proinflammatory genes such as IL-1β, COX-2, $PLA_2IV\alpha$. The activity of glycerophosphoinositol was particularly evident during the onset (time 4 h) and the full inflammmation (14 h). Glycerophosphoinositol also affected the expression of IκB-α, the prototypic target gene of transcription factor NF-κB. These preliminary results suggest an immunomodulatory role for glycerophosphoinositol. On the other hand, glycerophosphoinositol favoured the expression of anti-inflammatory genes such as IL-1Rα, IL-1RII, both of them antagonizing the proinflammatory activity of IL-1β.
Figure 15:
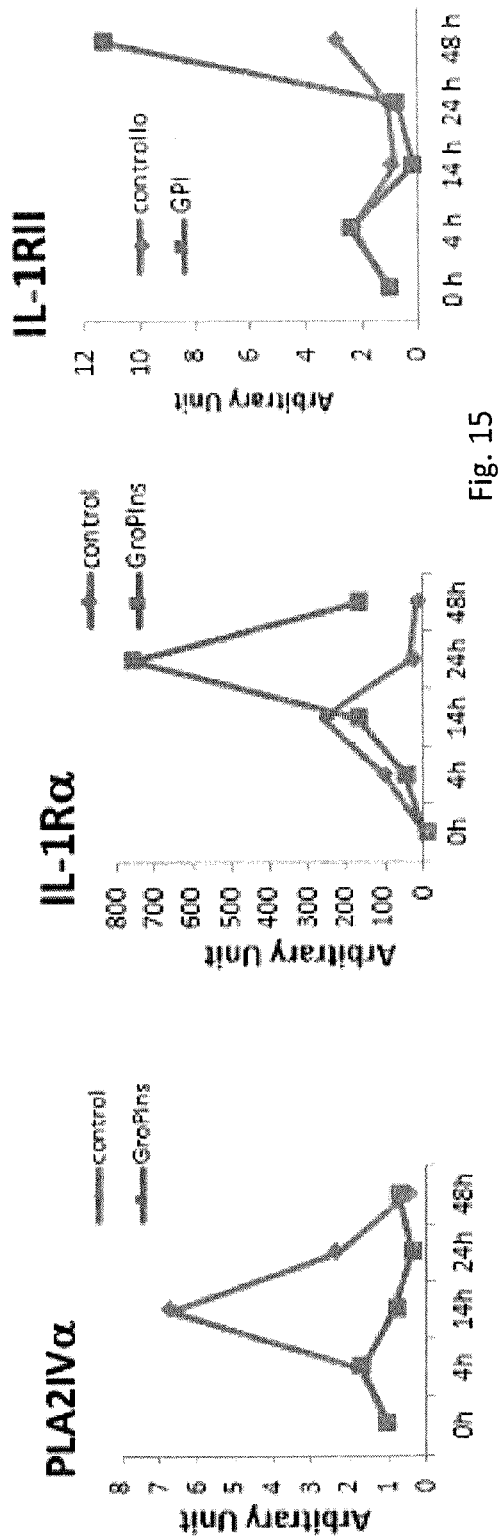
Figure 16:
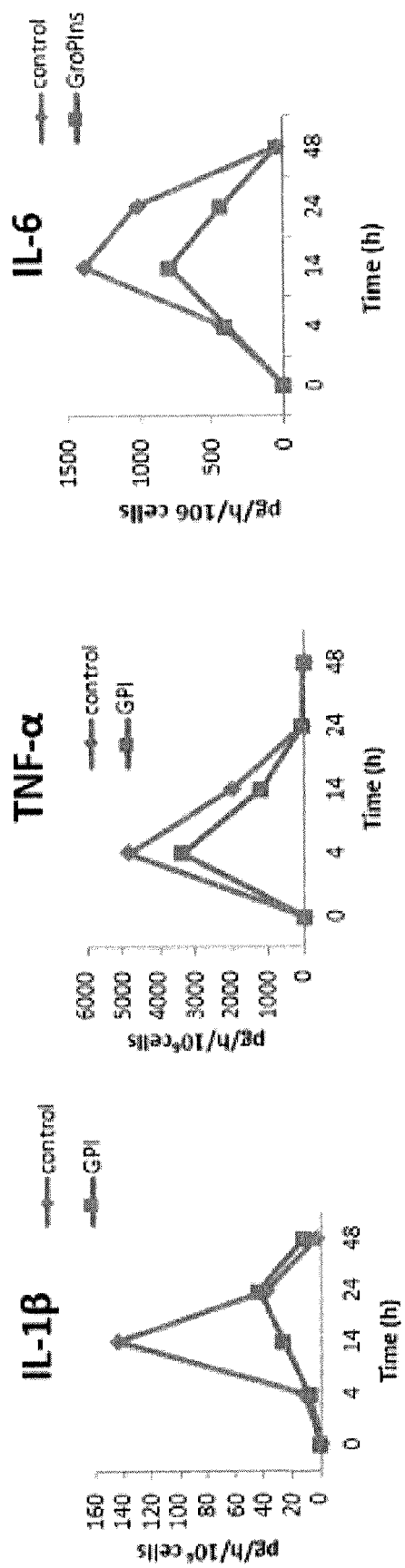
FIG. 16—Glycerophosphoinositol inhibits the release of cytokines. Human monocytes were purified from one donor and treated according to the in vitro model of human inflammation, previously described, in absence (blue line) or in presence (red line) of 300 μM glycerophosphoinositol. In detail, glycerophosphoinositol was added to cultured cells 20 minutes before LPS, IL-10 and TGF-β, that is, again after each wash. The growth medium was collected at time 4 h, 14 h, 24 h, 48 h; growth medium from freshly isolated monocytes was considered as control at time 0 h. The levels of cytokines Interleukin 1β (IL-1β), Tumor necrosis factor α (TNFα) and Interleukin-6 (IL-6) in the supernatants were measured by enzyme-linked immunosorbent assay (ELISA kit, R&D System) according to manufacturer's protocol. An increased release of these cytokines was observed during the full inflammation (time 4 h and 14 h) as expected. Glycerophosphoinositol significantly reduced the amount of these cytokines in the supernatants, confirming its immunomodulatory activity during the full inflammation.

Upon exposure to LPS, TNFα and IFN-γ human monocytes become activated in inflammatory macrophages and release pro-inflammatory cytokines, such as interleukin 1β (IL-1β), interleukin 6 (IL-6), tumor necrosis factor α (TNFα) which trigger and amplify the inflammatory reaction, and undergo inflammation-induced death (pyroptosis). Interestingly the exposure of cells to glycerophosphoinositol during the inflammatory process decreased the inflammatory phenotype and exerted a protective function against cell death. Indeed, as assessed by light microscopy investigation, in presence of glycerophosphoinositol the cellular viability increased (FIG. 14). According to this macroscopic observation, the expression profile of a panel of inflammatory genes revealed a strong immunomodulatory effect of glycerophosphoinositol, whose presence decreased the expression of some prototypic pro-inflammatory cytokines such as IL-1β and cyclooxygenase 2 (COX-2), as shown in FIG. 15. The same reduction was observed in the expression of PLA$_2$IVα gene, which catalyzes the synthesis not only of glycerophosphoinositols but also of arachidonic acid, which can be metabolized to pro-inflammatory eicosanoids. The effect of glycerophosphoinositol seemed to be exerted mainly during the onset (time 4 h) and the acute phase of inflammation (14 h) allowing us to suppose a role for this compound in counteracting the pro-inflammatory signaling originating from LPS. On the other hand, the expression of some antagonist cytokines, such as interleukin-1 receptor antagonist (IL-1Ra) or interleukin-1 receptor II (IL-1RII), which are responsible for the resolution of inflammatory response, increased early upon glycerophosphoinositol exposure. This inhibitory effect also extended on the release of cytokines; the levels of IL-1β, TNFα and IL-6 in the supernatants were measured and an increased release of these cytokines was observed during the full inflammation (time 4 h and 14 h) as expected. Glycerophosphoinositol significantly reduced the amount of these cytokines in the supernatants, confirming its immunomodulatory activity during the acute phase of inflammation (FIG. 16).

Because the genes modulated by glycerophosphoinositol were common target of NF-κB transcription factor, which in turn has a key role in coordinating the inflammatory response, the effect of glycerophosphoinositol on the activation of NF-κB has been evaluated. The activation of NF-κB is strongly linked to the phosphorylation and proteasomal degradation of its inhibitor IκB-α which, in unstimulated cells, sequester NF-κB into the cytosol preventing it to enter the nucleus. The proteasomal degradation of IκB-α mediated by the phosphorylation induced by pro-inflammatory stimuli frees NF-κB allowing it to enter the nucleus and bind to promoter of its target genes. One of the early genes regulated by NF-κB is IκB-α, which is then considered the canonical transcription target of NF-κB. The expression profile analysis of IκB-α revealed a modulation in the transcriptional kinetic of this gene in presence of glycerophosphoinositol.

In summary, these data are supportive for an active role of glycerophosphoinositol during the inflammatory response. In particular, glycerophosphoinositol has been shown to affect the onset and the acute phase of inflammation, probably affecting the transcription function of NF-κB into the nucleus. Actually, the mechanism underlying the gene expression inhibition induced by glycerophosphoinosotol deserves further investigations. The relevance of glycerophosphoinositol as compound for treatment of inflammatory diseases is strengthened by its capability to shape an anti-inflammatory microenvironment directly targeting pro-inflammatory mediators (cytokines), affecting inflammation-related transcription factors (NFkB), deactivating inflammatory cells (monocytes). Moreover, unlike other anti-inflammatory drugs, the small and water-soluble glycerophosphoinositol are actually safe and without toxic effects.

The invention claimed is:

1. A method for treating or reducing the severity of a symptom of sepsis, severe sepsis or septic shock related to a Lipopolysaccharide (LPS)-activated pro-coagulant tissue-factor (TF) activity, comprising administering a therapeutically effective amount of a Glycerophosphoinostitol (GPI) or derivative thereof to inhibit pro-coagulant TF activity in a mammal in need thereof, wherein said sepsis, severe sepsis or septic shock is not mediated by an activation or over-stimulation of cPLA$_2$, PLA$_2$IVα or any other isoform.

2. The method according to claim 1, wherein treating or reducing is for the severity of a symptom of sepsis, severe sepsis or septic shock related to a Lipopolysaccharide (LPS)-activated tissue-factor (TF) activity.

3. The method according to claim 1, wherein said sepsis, severe sepsis or septic shock is induced by high bacteremia.

4. The method according to claim 1, wherein the derivative is glycerophosphoinositol 4-phosphate (GroPIns4P) or glycerophosphoinositol 4,5-bisphosphate (GroPIns4,5P$_2$).

5. The method according to claim 1, wherein the symptom of sepsis, severe sepsis or septic shock related to a Lipopolysaccharide (LPS)-activated pro-coagulant tissue-factor (TF) activity comprises a disorder of coagulation and/or a disseminated intravascular coagulation.

6. The method according to claim 1 wherein the glycerophosphoinositol or derivative thereof is administered to a mammal in one or more of the following periods:
(a) prior to the onset of sepsis;
(b) during initial sepsis but before the onset of severe sepsis;
(c) during severe sepsis but before the onset of septic shock; and
(d) after the onset septic shock.

* * * * *

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: primer TF forward

<400> SEQUENCE: 1
cagtgattcc ctcccgaaca                                                  20

<210> SEQ ID NO 2
<211> LENGTH: 23
<212> TYPE: DNA
<213> ORGANISM: Artificial Sequence
<220> FEATURE:
<223> OTHER INFORMATION: primer TF reverse

<400> SEQUENCE: 2
tgcctttcta caactgtgta gag                                              23

<210> SEQ ID NO 3
<211> LENGTH: 22
<212> TYPE: DNA
<213> ORGANISM: Artificial Sequence
<220> FEATURE:
<223> OTHER INFORMATION: primer TNFa forward

<400> SEQUENCE: 3
gctgatggcc ctaaacagat ga                                               22

<210> SEQ ID NO 4
<211> LENGTH: 19
<212> TYPE: DNA
<213> ORGANISM: Artificial Sequence
<220> FEATURE:
<223> OTHER INFORMATION: primer TNFa reverse

<400> SEQUENCE: 4
cagagggcag aggtccagg                                                   19

<210> SEQ ID NO 5
<211> LENGTH: 22
<212> TYPE: DNA
<213> ORGANISM: Artificial Sequence
<220> FEATURE:
```

<223> OTHER INFORMATION: primer IL-1b forward

<400> SEQUENCE: 5
gctgatggcc ctaaacagat ga            22

<210> SEQ ID NO 6
<211> LENGTH: 19
<212> TYPE: DNA
<213> ORGANISM: Artificial Sequence
<220> FEATURE:
<223> OTHER INFORMATION: primer IL-1b reverse

<400> SEQUENCE: 6
aggcttgtca ctcggggtt            19

<210> SEQ ID NO 7
<211> LENGTH: 23
<212> TYPE: DNA
<213> ORGANISM: Artificial Sequence
<220> FEATURE:
<223> OTHER INFORMATION: primer COX-2 forward

<400> SEQUENCE: 7
ttccagatcc agagctcatt aaa            23

<210> SEQ ID NO 8
<211> LENGTH: 17
<212> TYPE: DNA
<213> ORGANISM: Artificial Sequence
<220> FEATURE:
<223> OTHER INFORMATION: primer COX-2 reverse

<400> SEQUENCE: 8
ccggagcggg aagaact            17

<210> SEQ ID NO 9
<211> LENGTH: 23
<212> TYPE: DNA
<213> ORGANISM: Artificial Sequence
<220> FEATURE:
<223> OTHER INFORMATION: primer GAPDH forward

<400> SEQUENCE: 9
caactttggt atcgtggaag gac            23

<210> SEQ ID NO 10
<211> LENGTH: 21
<212> TYPE: DNA
<213> ORGANISM: Artificial Sequence
<220> FEATURE:
<223> OTHER INFORMATION: primer GAPDH reverse

<400> SEQUENCE: 10
acagtcttct gggtggcagt g            21

<210> SEQ ID NO 11
<211> LENGTH: 21
<212> TYPE: DNA
<213> ORGANISM: Artificial Sequence
<220> FEATURE:
<223> OTHER INFORMATION: oligonucleotide containing the NF-KB binding
      site

<400> SEQUENCE: 11
agttgagggg atttcccagg c            21

```
<210> SEQ ID NO 12
<211> LENGTH: 20
<212> TYPE: DNA
<213> ORGANISM: Artificial Sequence
<220> FEATURE:
<223> OTHER INFORMATION: Primer COX2-F

<400> SEQUENCE: 12
tccaaacaca gtgcactaca                                            20

<210> SEQ ID NO 13
<211> LENGTH: 20
<212> TYPE: DNA
<213> ORGANISM: Artificial Sequence
<220> FEATURE:
<223> OTHER INFORMATION: primer COX2-R

<400> SEQUENCE: 13
ggtggactgt caatcaaatg                                            20

<210> SEQ ID NO 14
<211> LENGTH: 20
<212> TYPE: DNA
<213> ORGANISM: Artificial Sequence
<220> FEATURE:
<223> OTHER INFORMATION: primer PLA24alpha-F

<400> SEQUENCE: 14
tttacggtag tggtgttacg                                            20

<210> SEQ ID NO 15
<211> LENGTH: 20
<212> TYPE: DNA
<213> ORGANISM: Artificial Sequence
<220> FEATURE:
<223> OTHER INFORMATION: primer PLA24alpha-R

<400> SEQUENCE: 15
ctgtcagggg ttgtagagat                                            20

<210> SEQ ID NO 16
<211> LENGTH: 20
<212> TYPE: DNA
<213> ORGANISM: Artificial Sequence
<220> FEATURE:
<223> OTHER INFORMATION: primer IkBalpha-F

<400> SEQUENCE: 16
aaggctacca actacaatgg                                            20

<210> SEQ ID NO 17
<211> LENGTH: 19
<212> TYPE: DNA
<213> ORGANISM: Artificial Sequence
<220> FEATURE:
<223> OTHER INFORMATION: primer IkBalpha-R

<400> SEQUENCE: 17
tgagcattga catcagcac                                             19

<210> SEQ ID NO 18
<211> LENGTH: 20
<212> TYPE: DNA
<213> ORGANISM: Artificial Sequence
<220> FEATURE:
<223> OTHER INFORMATION: primer IL-1beta-F
```

```
<400> SEQUENCE: 18
gatgcacctg tacgatcact                                              20

<210> SEQ ID NO 19
<211> LENGTH: 20
<212> TYPE: DNA
<213> ORGANISM: Artificial Sequence
<220> FEATURE:
<223> OTHER INFORMATION: primer IL-1beta- R

<400> SEQUENCE: 19
gacatggaga acaccacttg                                              20

<210> SEQ ID NO 20
<211> LENGTH: 20
<212> TYPE: DNA
<213> ORGANISM: Artificial Sequence
<220> FEATURE:
<223> OTHER INFORMATION: primer IL-1Ralpha- F

<400> SEQUENCE: 20
gaggaggaga aggtgaagac                                              20

<210> SEQ ID NO 21
<211> LENGTH: 20
<212> TYPE: DNA
<213> ORGANISM: Artificial Sequence
<220> FEATURE:
<223> OTHER INFORMATION: primer IL-1Ralpha-R

<400> SEQUENCE: 21
cttctggtta acatcccaga                                              20
```